(12) United States Patent
Brennan et al.

(10) Patent No.: US 7,118,921 B1
(45) Date of Patent: Oct. 10, 2006

(54) INCORPORATION AND APPLICATIONS OF BIOMOLECULAR INTERACTIONS WITHIN A CARRIER

(75) Inventors: John D. Brennan, Dundas (CA); Christopher V. W. Hogue, Oakville (CA)

(73) Assignee: McMaster University, Hamilton (CA)

( * ) Notice: Subject to any disclaimer, the term of this patent is extended or adjusted under 35 U.S.C. 154(b) by 786 days.

(21) Appl. No.: 09/599,870

(22) Filed: Jun. 23, 2000

Related U.S. Application Data

(60) Provisional application No. 60/207,204, filed on May 26, 2000, provisional application No. 60/140,713, filed on Jun. 24, 1999.

(51) Int. Cl.
    *G01N 33/543* (2006.01)

(52) U.S. Cl. ............. 436/518; 436/523; 436/525; 436/528; 435/7.1; 428/402; 428/402.21; 428/403; 428/406; 422/55

(58) Field of Classification Search ............. 436/518, 436/523, 525, 528; 435/7.1; 428/402, 402.21, 428/403, 406; 422/55
    See application file for complete search history.

(56) References Cited

U.S. PATENT DOCUMENTS

| | | | |
|---|---|---|---|
| 4,959,301 A * | 9/1990 | Weaver et al. ............ 435/5 |
| 5,290,703 A * | 3/1994 | Hsu et al. ............ 436/71 |
| 5,603,960 A * | 2/1997 | O' Hagan et al. | |
| 5,679,377 A * | 10/1997 | Bernstein et al. | |
| 5,817,327 A * | 10/1998 | Ducheyne et al. ........ 424/425 |
| 5,866,322 A * | 2/1999 | Jou et al. | |
| 6,022,748 A * | 2/2000 | Charych et al. ............ 436/527 |
| 6,074,673 A * | 6/2000 | Guillen | |
| 6,277,413 B1 * | 8/2001 | Sankaram | |
| 6,312,731 B1 * | 11/2001 | Staas et al. | |
| 6,312,916 B1 * | 11/2001 | Kopetzki et al. ............ 435/7.5 |
| 6,395,299 B1 * | 5/2002 | Babich et al. ............. 424/484 |

FOREIGN PATENT DOCUMENTS

| EP | 0 071 704 A2 | 2/1996 |
| WO | WO 96/03117 A1 | 2/1996 |
| WO | WO 96/21628 | 7/1996 |
| WO | WO 99/07777 A1 | 2/1999 |

OTHER PUBLICATIONS

Bayer et al. "Avidin column as a highly efficient and stable alternative for immobilization of ligands for affinity chromatography". Journal of Molecular Recognition (1990), 3(3), 102-7. □□.*

Eisen et al. "Biotin-labeled and photoactivatable aldosterone and progesterone derivatives as ligands for affinity chromatography . . . " Euporopean Journal of Biochemistry (1996), 237(2), p. 514-18.*

Gray et al. "Secretion capture and report web: use of affinity derivatized agarose microdroplets for the selection of hydridoma cells", 1995 Journal of Immunological Methods, 182, pp. 155-163.*

* cited by examiner

*Primary Examiner*—James Housel
*Assistant Examiner*—Pensee T. Do
(74) *Attorney, Agent, or Firm*—Patricia Folkins

(57) ABSTRACT

Described is a carrier having a biomolecular interaction incorporated therein. The carrier is described as comprising a silica based glass and in an embodiment is a sol-gel derived glass. Also described are methods of incorporating biomolecular interaction within a carrier of the invention. Various types of biomolecular interaction are discussed as well as applications of carriers containing one or more biomolecular interactions.

20 Claims, 22 Drawing Sheets

FIGURE 7A-B
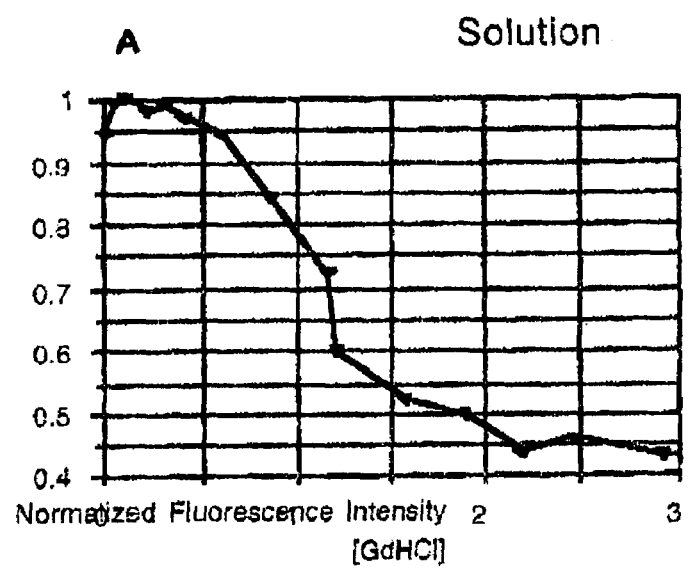
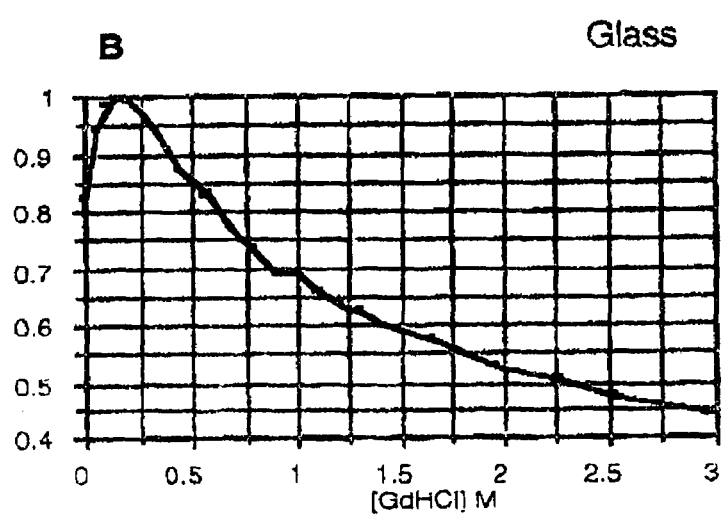

FIGURE 8A-B
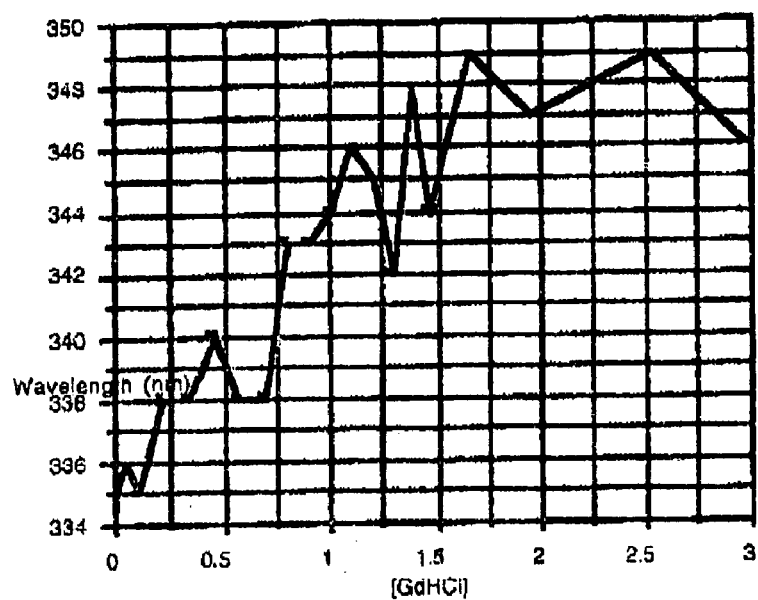
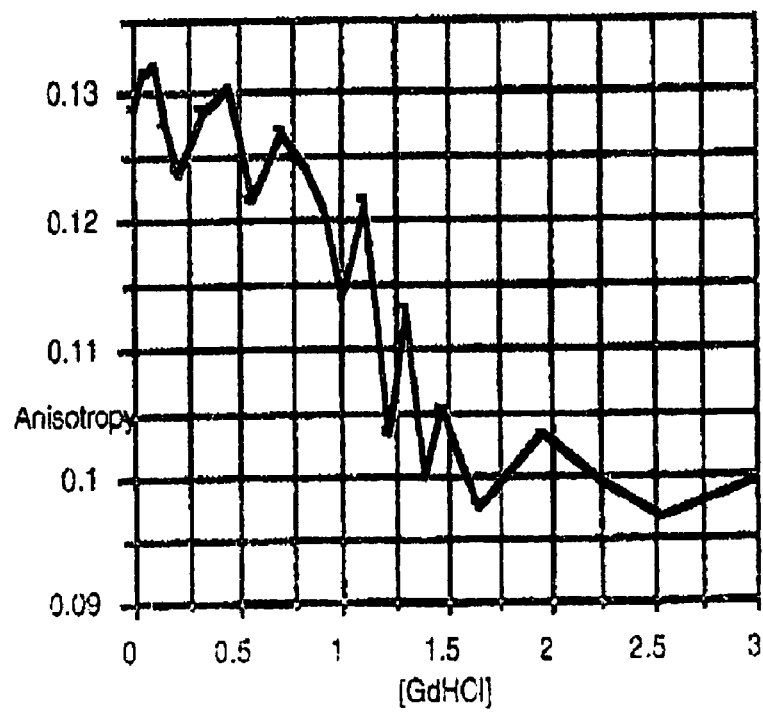

FIGURE 10A-B
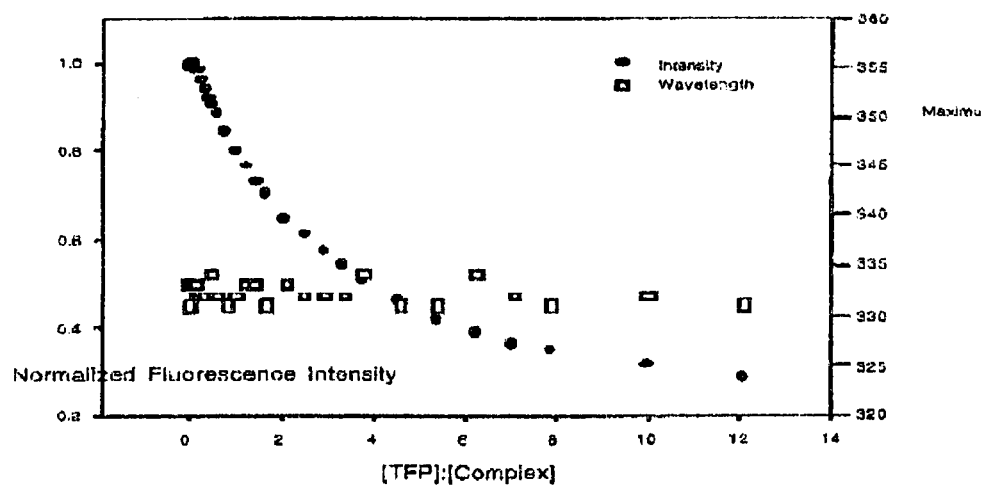
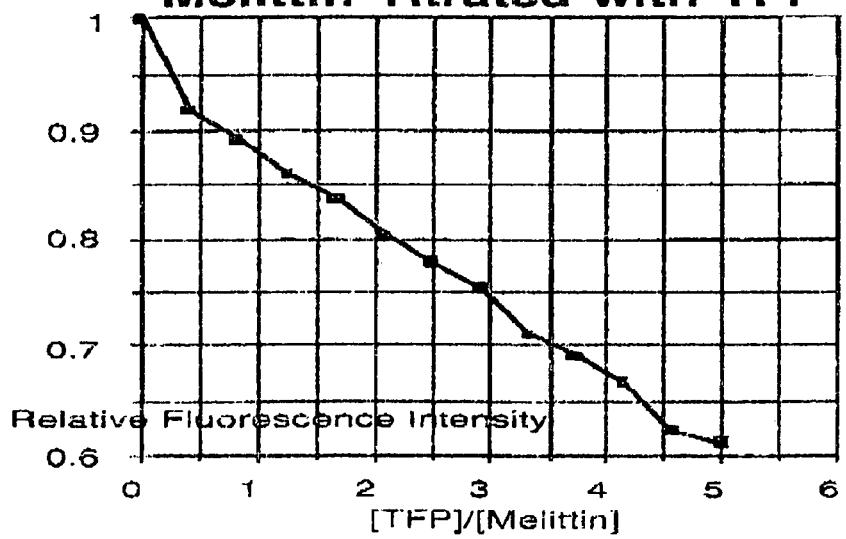

FIGURE 12

Proof of Concept of the Assay

|  | Anisotropy | Wavelength (nm) |
|---|---|---|
| Solution | 0.127 | 335 |
| Native | 0.129 | 334 |
| Denatured | 0.099 | 346 |
| Recovered | 0.136 | 331 |
| Denatured | 0.115 | 346 |
| Recovered with TFP | 0.121 | 346 |

FIGURE 14

Donor attached to Protein A, Acceptor attached to Protein B

Efficiency of energy transfer (E) related to distance (r) by; $\dfrac{R_0^6}{R_0^6 + r^6}$

- Use donor molecule which absorbs at longer $\lambda$ to TFP $\therefore$ avoid exciting TFP

FIGURE 15

Melittin
- Energy Donor
- Dansyl Chloride
- Absorbs @ 370nm
- Emits @ 500nm

BCaM
- Energy Acceptor
- Fluorescein derivative
- Absorbs @ 494nm
- Emits @ 518nm $$R_0 = 3.3 - 4.1 \text{ nm}$$

FIGURE 21
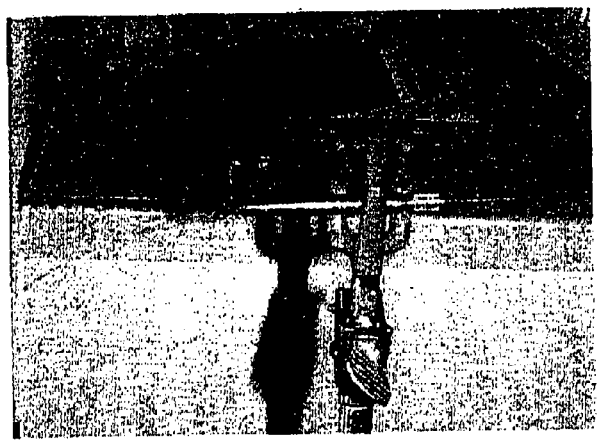
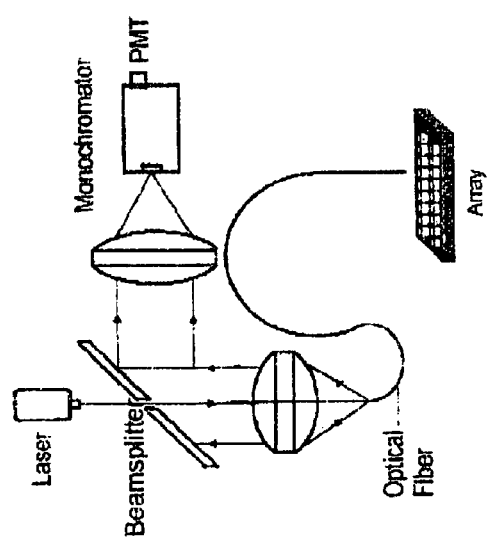

INCORPORATION AND APPLICATIONS OF BIOMOLECULAR INTERACTIONS WITHIN A CARRIER

This application claims the benefit of U.S. Provisional Patent Application No. 60/140,713 filed Jun. 24, 1999 and U.S. Provisional Patent Application No. 60/207,204 filed May 26, 2000.

FIELD OF THE INVENTION

The present invention is in the field of molecular interactions and is concerned with a means for containing such interactions, more particularly it relates to one or more biomolecular interactions within a carrier, methods for incorporating biomolecular interactions within a carrier, and uses of the biomolecular interactions within a carrier.

BACKGROUND OF THE INVENTION

Cells organize and regulate their growth, metabolism, differentiation and survival based, in large part, on external cues or signals such as hormones, growth factors, or molecules presented by neighbouring cells or the external environment. Interactions of proteins with ligands such as other proteins, phospholipids and nucleic acids mediate the internal responses to these external signals. Proteins that regulate intracellular function are generally, but not always, composed of modular domains that regulate protein—protein, protein-phospholipid, and protein-nucleic acid interactions.

A protein modular domain is a sequence of about 50 to 100 amino acids characterized by an ability to fold into the appropriate three-dimensional structure, and to retain its intermolecular binding properties, even in the absence of additional linked polypeptide sequences. A large number of protein modules have been identified. For example, protein modules have been identified that are involved with (i) cellular functions that control cell growth, or induce cell death or inflammation; (ii) the development of the cytoskeleton; (iii) the intracellular anti-microbial machinery of the cell; and (iv) transcriptional assembly.

With the increasing discovery of new protein—protein interactions there is a need for assays to analyze the interactions and identify modulators of the interactions. However, interacting protein domains are inherently difficult to assay. For example, the identification of inhibitors of an interaction may require a thermodynamically unfavorable situation wherein a weakly binding compound must disrupt and then binds to the interface between two tightly bound protein monomers. Therefore, there is a need for effective methods for assaying biomolecular interactions and for identifying substances that modulate the interactions.

SUMMARY OF THE INVENTION

The present invention contemplates a biomolecular interaction physically entrapped or covalently attached within a carrier, preferably a solid carrier.

The invention also contemplates a solid support for a biomolecular interaction comprising silica based glass or a hybrid organic-inorganic glass matrix or an organic glass matrix (collectively referred to as a silica based glass) having a biomolecular interaction incorporated within the matrix, either by physical entrapment or covalent attachment.

Accordingly, in one embodiment the present invention provides a carrier for containing a biomolecular interaction, said carrier comprising inorganic, organic or organic and inorganic material, preferably the biomolecular interaction is incorporated within a matrix of the carrier.

According to another embodiment the present invention provides a carrier containing a biomolecular interaction, said carrier comprising inorganic, organic or organic and inorganic material, preferably the biomolecular interaction is incorporated within a matrix of the carrier, more preferably the carrier comprises a silica based glass.

According to another embodiment the material of a carrier according to the invention is a silicon, titanium, vanadium or cerium-based metal alkoxide, alkylated metal alkoxide or otherwise functionalized metal alkoxide or a corresponding metal chloride, silazane, polyglycerylsilicate or other silicate precursor. Preferably the carrier is derived by a sol-gel processing method.

According to another embodiment the present invention provides a carrier containing a biomolecular interaction wherein the biomolecular interaction is bioactive. According to another embodiment the carrier is also bioactive, preferably either bioactive form is pre-treated to contain components found in an animal fluid, preferably the pre-treatment is by immersion in a solution containing components found in an animal fluid for a period of up to about seven days prior to use. According to one embodiment of this aspect of the invention the animal fluid is interstitial fluid. Preferably such carrier is synthesized under sterile conditions or sterilized subsequent to synthesis using conventional sterilization methods.

In another embodiment of this bioactive aspect of the biomolecular interaction, where the carrier may also be bioactive, the carrier provides controlled release of the biologically active biomolecular interaction over time.

In another aspect, the invention relates to a carrier containing reactive functional groups that can covalently bond to reactive groups of the biomolecular interaction to form a permanent anchor to prevent leaching of the interaction. In an embodiment, aminopropyltriethoxysilane may be incorporated into the glass as a silane precursor, activated with glutaraldehyde and allowed to react with the amino groups of lysine residues within the protein to form amide bonds between the carrier and the protein. Many other reactions can also be done, and would be obvious to someone skilled in the art.

In another aspect of the invention there are provided methods of preparing the carrier and the biomolecular interaction incorporated in the carrier.

According to one embodiment of this aspect of the invention there is provided a method for preparing a carrier having a biomolecular interaction incorporated within the carrier comprising:

(a) reacting a reactant comprising a functionalized metal alkoxide or a corresponding or other silicate precursor with water;

(b) adjusting the pH to a value between 4 and 10 either before or during the addition of an aqueous solution containing a biomolecular interaction to provide a mixture;

(c) casting the mixture;

(d) allowing the mixture to gel and age; and (e) partially drying the aged gel.

Preferably the reaction occurs alone or as mixtures of more than one reactant where the reactant is a silicon, titanium, vanadium or cerium-based metal alkoxide, alkylated metal alkoxide or otherwise functionalized metal alkoxide, more preferably the functionalized metal alkoxide is aminopropyl triethoxysilane. In another embodiment the corresponding functionalized metal alkoxide is metal chloride, silazane, or polyglycerylsilicate, and in another embodiment the reacting occurs in an acidic or basic aqueous medium. For these embodiments of methods of the invention preferably the reactant and water are in a molar ratio of from about 1:1 to about 20:1 water/reactant.

According to another embodiment of the method the casting of the mixture is in a mold, a column, a microtiter well, a spot on a surface by pin spotting, ink jet deposition or screen printing; or a film on a surface by dipcasting, spin-casting or spraying.

According to another embodiment of the method the gel and aging is at temperatures from about 0° C. up to about 40° C.

According to yet another embodiment the partial drying is at temperatures from about 4° to about 40° C.

In another aspect of the invention there is provided a method for the preparation of a carrier having a bioactive biomolecular interaction incorporated in the carrier.

(a) reacting alone or as mixtures a silicon, titanium, vanadium or cerium-based metal alkoxide, alkylated metal alkoxide or otherwise functionalized metal alkoxide (such as aminopropyl triethoxysilane) or a corresponding metal chloride with water in a molar ratio of from about 1:1 to about 20:1 water/metal alkoxide (or metal chloride) in an acidic or basic aqueous medium;

(b) adjusting the pH to a value between 4 and 10 either before or during the addition of an aqueous solution containing the molecules that comprise the biomolecular interaction;

(c) casting the mixture into a mold, as a thin film on a surface via dipcasting, spin-casting or spraying, in a microtiter well, or as a spot on a surface via pin spotting, inkjet deposition or screen printing (d) allowing the mixture to gel and age at temperatures from about 0° C. up to about 40° C.; and partially drying the aged gel at temperatures from about 4° to about 40° C.

In another aspect of the invention there is provided a method for the preparation of a carrier having a bioactive bimolecular interaction incorporated in the carrier.

According to one embodiment of this aspect, the method comprises:

(a) incorporating the bioactive biomolecular interaction in a carrier;

(b) hydrolysis and polycondensation of at least one monomer to provide a solid matrix bonding the bioactive biomolecular interaction which is incorporated in the carrier; and (c) imparting mechanical, chemical and thermal stability in the matrix.

Preferably the at least one monomer is a functionalized or non-functionalized alkoxysilane; functionalized or non-functionalized bis-silane; functionalized or non-functionalized chlorosilane; sugar, polymer, polyol or amino acid substituted silicate; or additives selected from any available organic polymer, polyelectrolyte, sugar (natural or synthetic) or amino acids (natural and non natural).

In another embodiment the monomer is based on titanium, vanadium or cerium.

In yet another embodiment of a method according to this aspect of the invention mechanical, chemical and thermal stability of the matrix is imparted by combination of precursors and additives. Preferably the mechanical, chemical and thermal stability is imparted by combination of precursors and/or additives, and by choice of aging and drying methods. Preferably the carrier comprises a silica based glass, more preferably a silicon, titanium, vanadium or cerium-based metal alkoxide, alkylated metal alkoxide or otherwise functionalized metal alkoxide or a corresponding metal chloride, silazane, polyglycerylsilicate or other silicate precursor.

In another embodiment of the method the carrier is derived by a sol-gel processing method, and preferably the carrier is bioactive.

In yet another aspect of the invention there is provided a method of treating an animal with a carrier and a biomolecular interaction of the invention. According to one embodiment the method comprises administering an effective amount of a biologically active biomolecular interaction contained in a carrier such that the animal is thereby treated. Preferably the treating is by site-specific targeting in the animal. More preferably the effective amount of a biologically active biomolecular interaction is a chemotherapeutic for treating cancer.

In a further aspect of the present invention there is provided a method for screening a compound or substance to determine the degree of inhibition or binding of a biomolecular interaction in a carrier of the invention.

According to one embodiment the method for screening a compound or substance to determine the degree of inhibition or binding of a biomolecular interaction by the compound or substance comprises contacting the compound or substance to be tested with the molecules of a biomolecular interaction wherein the molecules are incorporated within a carrier and they are capable of forming a biomolecular interaction in the carrier, and wherein inhibition of the formation of the biomolecular interaction or binding by the compound or substance causes a change in the amount of a detectable signal produced by the molecules of the interaction of by one or more labels at or near the site of interaction of the molecules. Preferably the biomolecular interaction is incorporated within a matrix of the carrier, and the carrier comprises a silica based glass.

According to one embodiment the carrier is prepared from a silicon, titanium, vanadium or cerium-based metal alkoxide, alkylated metal alkoxide or otherwise functionalized metal alkoxide or a corresponding metal chloride, silazane, polyglycerylsilicate or other silicate precursor. Preferably the carrier is derived by a sol-gel processing method. More preferably the bimolecular interaction is bioactive. In another embodiment the carrier is bioactive.

According to another broad aspect the invention provides materials and methods of high throughput screening for compounds or substances which inhibit protein—protein interactions, but as will readily be appreciated, the methods and materials described herein may be used to assay any substance—substance interactions. In this respect the invention provides a method of high through put screening for a substance which inhibits or binds a biomolecular interaction. According to an embodiment of this aspect of the invention the method comprises the steps of:

(a) incorporating a biomolecular interaction within a carrier. Preferably the biomolecular interaction is a population of a purified protein comprising a binary protein—protein interacting pair is encapsulated in a carrier. This protein is preferably designed so that it has a solvent-sensitive fluorescent probe at or near the dimer interface or has one protein partner labelled with a fluorescence energy donor and the other protein partner labelled with a fluorescence energy acceptor to allow fluorescence resonance energy transfer (FRET) to occur between the protein partners, preferably in a distance-dependent manner.

(b) forming an array of sol-gel derived spots on a support wherein each spot contains a biomolecular interaction;

(c) measuring a signal from the interaction in the absence of any other substances; Preferably the initial fluorescence signal (intensity, emission wavelength, polarization and/or lifetime of a single probe, a donor and/or an acceptor) of this complex in the absence of any other compounds is first measured. The fluorescence signal indicates that the pair of proteins is in a complex.

(d) reversibly disrupting the biomolecular interaction such that the signal is detectably altered; Preferably the sample is sufficiently denatured (if necessary) to cause a reversible disruption of the binary protein—protein interaction, causing the signal of the reporter at the protein-interface or of the donor-acceptor pair to be significantly altered.

(e) the substance is added to the biomolecular interaction in the carrier, and reversing the disruption; and (f) measuring the signal; The denaturing conditions (if used) are reversed to cause the binary interacting system to reform in the sol-gel matrix. The original fluorescence signal of the attached probe or donor-acceptor pair is recovered if no disruption of the complex occurs (i.e., target is not a drug candidate). Where the original signal is not recovered, the substance is determined to bind or inhibit the biomolecular interaction. The substance is considered to have disrupted the protein—protein interaction, and can be tested further as, for example, a potential drug candidate.

In a preferred embodiment the signal generated by the assay is due to excitement by a He Cd laser through an optical fiber and the signal, preferably fluorescence, and is preferably detected through the same fiber, as shown in FIG. 21.

In another embodiment the signal is excited by a nitrogen laser through a bifurcated optical fiber and fluorescence is preferably detected through the same fiber and more preferably detected in a time-gated or time-resolved mode.

In another embodiment of the method signals generated by the array are excited by a laser, lamp or light emitting diode, either directly or through an optical fiber, and the signal, if any, preferably fluorescence, is detected using a CCD camera.

In still yet another aspect, the present invention provides a normal or frontal affinity chromatography method for pre-screening a compound based on incorporation of a biomolecular interaction or individual protein partners within a carrier into a column, addition of a denaturant, passing of individual compounds, mixtures or mixtures including an indicator ligand through the column in conjunction with removal of the denaturant (if present), and determination of retention behaviour using fluorescence, mass spectrometric or other detection methods.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

The invention will be better understood with reference to the drawings in which:

FIG. 7A is a graph illustrating emission intensity changes during GdHCl denaturation of the holo-BCaM-Mel complex in solution.

FIG. 7B is a graph illustrating emission intensity changes during GdHCl denaturation of the holo-BCaM-Mel complex entrapped in glass.

FIG. 8A is a graph illustrating emission wavelength changes during GdHCl denaturation of the holo BCaM-Mel complex when entrapped in glass.

FIG. 8B is a graph illustrating anisotropy changes during GdHCl denaturation of the holo BCaM-Mel complex when entrapped in glass.

FIG. 10A is a graph illustrating intensity and wavelength changes in the intact holo-BCaM-Mel complex caused by addition of the inhibitor TFP without a preliminary denaturation step.

FIG. 10B is a graph illustrating intensity changes when melittin is titrated with TFP

FIG. 12 is a table illustrating anisotropy and wavelength values obtained with an assay according to the present invention with BCaM:Melittin complex

FIG. 14 illustrates the application of FRET to an assay according to the present invention.

FIG. 15 illustrates a possible FRET system for BCaM-Melittin

FIG. 21 is a He—Cd laser based fiber optic fluorimeter for reading of sol-gel derived arrays.

DETAILED DESCRIPTION OF THE INVENTION

Types of Biomolecular Interactions

Figure 1:
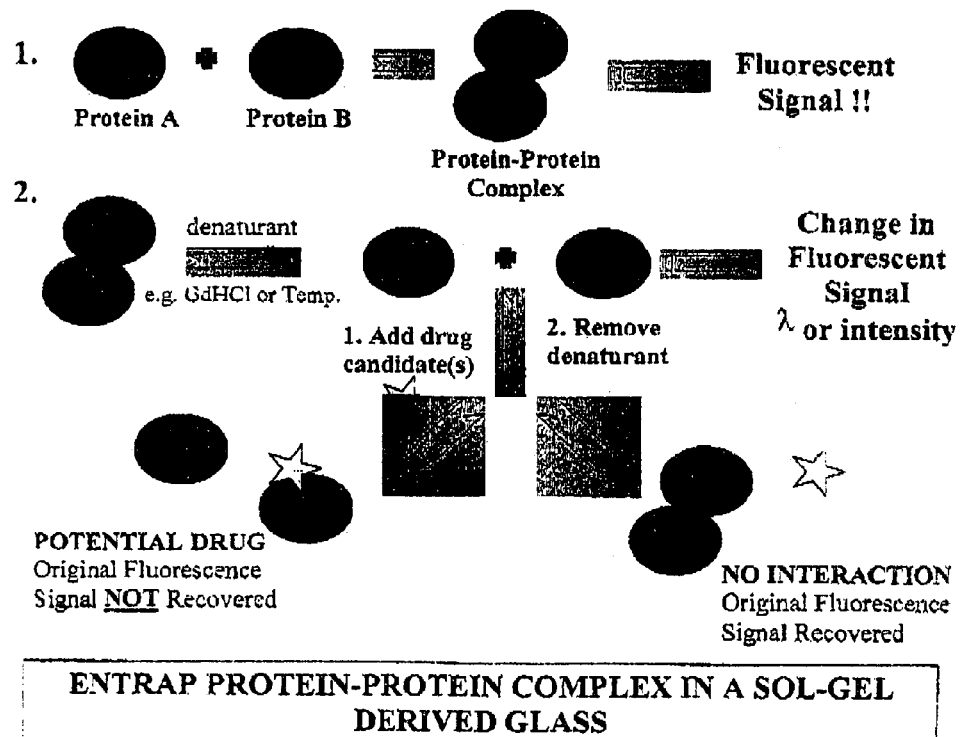
FIG. 1 is a schematic representation of the steps involved in an assay according to the present invention.

As mentioned above, the present invention contemplates a biomolecular interaction physically entrapped or covalently attached within a carrier, preferably a solid carrier.

As used herein, the expression "interfere with" and like expressions mean inhibiting, reducing, diminishing or blocking the interaction between the members of a biomolecular interaction.

The term "interaction" as used herein means the binding, association, or complexing of the members of a biomolecular interaction and includes intramolecular binding, association or complexing, regardless of the degree of association between molecules, or intra molecularly, however the association is formed.

The term "animal" as used herein includes all members of the animal kingdom including mammals, preferably humans.

Administration of an "effective amount" of the substances of the present invention is defined as an amount effective, at dosages and for periods of time necessary to achieve the desired result. The effective amount of a substance of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

As used herein the terms "biologically active" and "bio-active" mean the substance(s) or compound(s) in question exert(s) or is (or are) able to exert an effect in a biological organism.

The term "containing" as used herein means any form or type of integration, or incorporation such that the substance or substances, including biomolecular interaction, is/are able to be carried by a carrier.

As used herein a "biomolecular interaction" is a complex of two or more biological species (including proteins, polypeptides, peptides, amino acids, DNA, RNA, phospholipids, co-factors). Biomolecular interactions may comprise two or more interacting molecules including but not limited to a protein—protein interaction, a protein-nucleic acid interaction, a protein-phospholipid interaction, or a nucleic acid-nucleic acid interaction. A biomolecular interaction may comprise biomolecular complexes wherein each complex comprises two or more interacting molecules. It may be homodimeric (or of higher order, i.e., trimers, tetramers, etc.) or heterodimeric (or of higher order, i.e., trimers, tetramers etc.). This includes, but is not limited to, homodimeric proteins, heterodimeric proteins, supramolecular protein assemblies, double stranded DNA, DNA-protein interactions, DNA-RNA interactions, protein-lipid interactions, and other such combinations which would be readily apparent to those skilled in the art. Such complexes are held together by a variety of bonds, including but not limited to, ionic interactions, hydrogen bonds, van der Waal's interactions, hydrophobic interactions, dipole—dipole interactions, dipole-induced dipole interactions and induced dipole-induced dipole interactions.

Interacting molecules that form a biomolecular interaction that may be incorporated in a carrier in accordance with the invention include polypeptides, nucleic acids (DNA or RNA), and phospholipids (including sphingolipids, fatty acids, cholesterol and other steroids).

Any nucleic acid that is involved in, or encodes a polypeptide involved in transducing signals in a cell by interacting with a nucleic acid molecule or polypeptide may be a component of a biomolecular interaction of the present invention. The nucleic acid may be a polyribonucleotide or polydeoxribonucleotide, which may be unmodified RNA or DNA or modified RNA or DNA. A nucleic acid may be a single- or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. A nucleic acid used in the invention may include all of a nucleic acid molecule, but more typically involves only a region of a molecule that can interact with a nucleic acid, or polypeptide or region thereof.

A nucleic acid selected for use in the present invention may contain one or more modified bases. Thus, DNAs or RNAs with backbones modified for stability or for other reasons are "nucleic acids" as that term is intended herein. Moreover, DNAs or RNAs comprising unusual bases, such as inosine or 2-aminopurine, or modified bases, such as tritylated bases, to name just two examples, are nucleic acids as the term is used herein.

It will be appreciated that a great variety of modifications have been made to DNA and RNA that serve many useful purposes known to those of skill in the art. The term "nucleic acid" as it is employed herein embraces such chemically, enzymatically or metabolically modified forms of nucleic acids, as well as the chemical forms of DNA and RNA characteristic of viruses and cells, including simple and complex cells.

Any polypeptide that is involved in transducing signals in a cell by interacting with a nucleic acid molecule or polypeptide may be a component of a biomolecular interaction of the present invention. "Polypeptide" as used herein, refers to any protein or peptide comprising two or more amino acids joined to each other by peptide bonds or modified peptide bonds. The term refers to both short chains (i.e., peptides, oligopeptides and oligomers) and to longer chains (i.e., proteins).

A polypeptide used in the invention may include the entire polypeptide but more typically involves a modular domain that interacts with another molecule including a polypeptide or region thereof, or a nucleic acid or a region thereof. Typically, a modular domain is a sequence of about 50 to 100 amino acids characterized by an ability to fold into the appropriate three-dimensional structure, and to retain its intermolecular binding properties, even in the absence of additional linked polypeptide sequences. A modular domain may be a sequential portion of a polypeptide, i.e., a contiguous sequence of amino acids, or it may be conformational, i.e., a combination of non-contiguous sequences of amino acids which when the molecule is in its native state forms a structure that interacts with another molecule.

A large number of protein modular domains have been identified. For example, protein modular domains have been identified that are involved with (i) cellular functions that control cell growth, or induce cell death or inflammation; (ii) the development of the cytoskeleton; (iii) the intracellular anti-microbial machinery of the cell; and (iv) transcriptional assembly. Examples of modular domains include, but are not limited to, the Src homology 2 (SH2) domain, Src homology 3 (SH3) domain, phosphotyrosine binding (PTB) domain, discs large protein (PDZ) domain, plectstrin homology (PH) domain, sterile-alpha-motif (SAM) domain, and F-box motif domain.

Examples of proteins containing protein modules that may be used in the invention include, but are not limited to, GAP, Fps, Src, Abl, PLCγ, v-Crk, Nck, p85 P13K, tensin, Vav, c-Yes, Fgr, Fyn, Lck, Lyn Hck, SHIP1, SHIP2, and Blk, (SH2), Abl, PLCγ, Grb2, v-Src, spectrin, P13-kinase subunit p85, Ras-GAP, Crk, Nck, myosin1B, fodrin, ABP-1, SHIP1, and SHIP2 (SH3), SHIP1, SHIP2, Fe65L2, Shc, X11 proteins, Cbl, Sck, internal ribosome entry sites, PHIP, Dok-R (PTB), insulin and insulin-like growth factor (PTB and PH), X11 proteins, Af6, GRIP, syntenin, and FAP-1 (PDZ), serine/threonine protein kinases, cytoplasmic scaffolding and adapter scaffolding and adapter proteins, regulators of lipid metabolism, the GTPases, members of the ETS family of transcription factors, TEL, and Tankyrase (SAM), and cdc4, Grr1, pop1, Met30, Scon2/Scon3 (F-box motif).

A polypeptide or portion thereof used in the present invention may contain amino acids other than the 20 amino acids commonly referred to as the 20 naturally occurring amino acids. Many amino acids, including the terminal amino acids, may be modified in a given polypeptide used in the present invention, either by natural processes, such as processing and other post-translational modifications, but also by chemical modification techniques which are well known to the art. By way of example, the use of the modified amino acid 7-azatryptophan is described herein.

The common modifications that occur naturally in polypeptides are too numerous to list exhaustively here, but they are well described in basic texts and in more detailed monographs, as well as in a voluminous research literature, and they are well known to those of skill in the art. Several particularly common modifications, glycosylation, lipid attachment, sulfation, gamma-carboxylation of glutamic acid residues, hydroxylation and ADP-ribosylation, for instance, are described in most basic texts, such as, for instance Proteins—Structure And Biomolecular Properties, 2nd Ed., T. E. Creighton, W.H. Freeman and Company, New York (1993). Many detailed reviews are available on this subject, such as, for example, those provided by Wold, F., Posttranslational Protein Modifications: Perspectives and Prospects, pgs. 1–12 in Posttranslational Covalent Modification Of Proteins, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663:48–62 (1992).

It will be appreciated, as is well known and as noted above, that polypeptides used in the present invention may not be entirely linear in their sequence. For instance, polypeptides that may be used for the present invention may be branched as a result of ubiquitination, and they may be circular, with or without branching, generally as a result of posttranslation events, including natural processing events and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

Without limitation, those variants of polynucleotides or polypeptides, or polynucleotides or polypeptides that differ from a reference polynucleotide or polypeptide may be used in the present invention. Generally, differences are limited so that the sequences of the reference and the variant are closely similar overall and, in many regions, identical. Changes in the nucleotide sequence of a variant may be silent. That is, they may not alter the amino acids encoded by the polynucleotide. Where alterations are limited to silent changes of this type a variant will encode a polypeptide with the same amino acid sequence as the reference polypeptide. Changes in the nucleotide sequence of a variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. A variant of a reference polypeptide may differ in amino acid sequence by one or more substitutions, additions, deletions, fusions and truncations, which may be present in any combination.

Mimetics of a polypeptide may also be used in the invention. Mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. Peptoids may also be used which are oligomers of N-substituted amino acids and can be used as motifs for the generation of chemically diverse libraries of novel molecules.

Any phospholipid that is involved in transducing signals in a cell by interacting with a nucleic acid molecule or polypeptide may be a component of a biomolecular interaction of the present invention. "Phospholipid", as used herein, refers to a molecule having a glycerol backbone covalently linked to two long, non-polar fatty acid hydrocarbon chains and comprising a variable phosphate-containing polar group. A phospholipid used in the invention may include the entire molecule but more typically involves a domain that interacts with another molecule (e.g. polypeptide or region thereof, or a nucleic acid or a region thereof). Examples of phospholipids that may be used in the present invention include but are not limited to phosphatidylcholine, phosphatidylserine, phosphatidylethanolamine, sphingomyelin, ceramide, phosphatidylinositol-4,5-biphosphate, phosphatidylinositol 4-phosphate, and sphingosine 1-phosophate.

The polypeptides, nucleic acids, phospholipids, and biomolecular complexes may be prepared using techniques known in the art. For example, proteins may be obtained as an isolate from natural cell sources, or they may be produced by recombinant procedures. Polypeptides may be purified for use in the present invention using high-throughput protein purification methods such as fluidized-bed chromatography. Polypeptides may also be prepared by chemical synthesis using techniques well known in chemistry such as solid phase synthesis (Merrifield, 1964, J. Am. Chem. Soc. 85:2149–2154) or synthesis in homogenous solution (Houbenweyl, 1987, Methods of Organic Chemistry, ed. E. Wansch, Vol. 15 I and II, Thieme, Stuttgart).

A nucleic acid that is DNA can be isolated by preparing a labeled nucleic acid probe based on all or part of the nucleic acid sequence and screening an appropriate DNA library (e.g. a cDNA or genomic DNA library). A nucleic acid that is DNA can also be isolated by selectively amplifying a nucleic acid sequence using for example polymerase chain reaction (PCR) technologies well known in the art (Dieffenbach, C. W. and G. S. Dveksler (1995) PCR Primer, a Laboratory Manual, Cold Spring Harbor Press, Plainview, N.Y.). A nucleic acid which is RNA can be isolated by cloning a cDNA encoding a protein into an appropriate vector which allows for transcription of the cDNA to produce an RNA molecule which encodes the protein. Nucleic acids may also be chemically synthesized using standard techniques. Methods of chemically synthesizing polydeoxynucleotides are known, including but not limited to solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Examples of biomolecular interactions which can be incorporated in a carrier in accordance with the invention include protein—protein interactions described in the Cell Signaling Networks Database (http://geo.nihs.go.jp/csndb/main.html) and protein-nucleic acid interactions described in The Transcription Factor Database (http://transfac.gbf-braunschweig.de/TRANSFAC), as well as protein-co-factor complexes. Particular examples of protein—protein interactions are the following: P13K-platelet derived growth factor (PDGFR), GAP-PDGFR, PLC-γ-PDGFR, PLC-γ- epidermal growth factor receptor (EGFR), c-Src-PDGFR, v-Src-PI3-kinase, Shc-EGFR, Shc-PGDF, Shc-Trk, Shc-Grb2, EGFR-Grb2, Grb2-Sos, EGFR-Grb2-Sos, IRS1-Grb2, IRS1-PI3 kinase, SAP-SLAM, GRF-2-CaM, Shc-SHIP, SHIP-Grb2, B class ephrin-GRIP, B class ephrin-PHIP, B class ephrin-syntenin, B class ephrin-FAP-1, Cdc34-Cdc53-Skp1, and CaM-melittin.

Labelling A Biomolecular Interaction

A biomolecular interaction may be selected or designed for use in the invention so that the disruption and/or reformation of the interaction may be detected. A biomolecular interaction can be designed so that it has one or more intrinsic labels at a site of interaction. For example, a biomolecular interaction that comprises an interacting polypeptide may be designed so that the polypeptide has a detectable amino acid or amino acid analogue at the site of interaction. For example, the polypeptide may have a native tryptophan residue at the site of interaction, or the residue may be inserted into the polypeptide at a site of the interaction. This latter approach is preferably used for small polypeptides that do not have a large number of native tryptophan residues.

An amino acid analogue such as the water sensitive fluorophore 7-azatryptophan (7AW), a highly specific tryptophan analogue, may be at the site of interaction. Such an analogue may be introduced into an interacting site of a polypeptide using known methods that permits the incorporation of the analogue. 7-azatryptophan is a non-natural amino acid that undergoes a solvent-dependent tautomerization reaction, which imparts a solvent-dependent quenching of the fluorescence of 7-azatryptophan in the presence of hydroxylated solvents (e.g. water or alcohols). When 7-azatryptophan has no water solvation, it has an intense, long-lived fluorescence with an emission maximum between 350–370 nm. This is typical of the intrinsic fluorescence spectrum of 7-azatryptophan incorporated polypeptides that have buried tryptophan residues. Denaturation and subsequent solvent exposure imparts a dramatic fluorescence quenching on 7-azatryptophan incorporated polypeptides, an intensity response that can be 5–20 fold, compared to the typical response of tryptophan, which changes less than 2-fold. The 7-azatryptophan fluorescence can be excited at wavelengths as great as 315 nm, beyond the normal absorbance of DNA or polypeptides, thus allowing exclusive detection of 7-azatryptophan fluorescence in the presence of other polypeptides or DNA.

A pair of interacting polypeptides with 7-azatryptophan residues at the polypeptide-interaction interface will have a strong 7-azatryptophan fluorescence that will become quenched as the interaction is disrupted. This phenomenon has been demonstrated in solution with the dimeric protein tryptophanyl-tRNA synthetase from *B. subtilis* that has a single tryptophan residue at the dimer-interface. Thermal or chemical denaturation of the 7-azatryptophan protein shows a two-state transition that shows first the dissociation of the subunits followed by their unfolding. The initial stage cannot be detected with tryptophan fluorescence.

A biomolecular interaction may also be extrinsically labelled at a site of interaction. One or more labels may be used and the label may be a fluorescent compound, phosphorescent compound, luminescent compound, or enzyme. Examples of labels include fluorescent compounds such as acrylodan, nitrobenzoxadiazole, fluorescein, rhodamine, and lanthanide phosphors, luminescent labels such as luminol; and enzymatic labels such as horseradish peroxidase, β-galactosidase, luciferase, alkaline phosphatase, and acetylcholinesterase.

In an embodiment of the invention comprising an interacting molecule that is a polypeptide, a single reactive cysteine residue can be placed within the polypeptide at a location that is at or near a site of interaction. Thiol selective probes such as acrylodan or iodoacetoxy-nitrobenzoxadiazole, can be attached to the reactive cysteine residue. The use of thiol selective probes has a number of advantages. It permits the extension of the invention to excitation wavelengths in the visible range, eliminating potential protein auto-fluorescence issues, and allowing the use of inexpensive instrumentation that does not require quartz or fused silica optics.

In another embodiment, the C- or N-terminus of the protein, or carboxylate or amino groups within the protein (i.e., glutamate, lysine) may be labelled with one or more carboxylate or amino reactive probes.

In yet another embodiment, one interacting partner may be labelled with a fluorescence energy transfer donor (organic or lanthanide based) and the other interacting partner with a fluorescence energy transfer acceptor, using one or more of the methods listed above. The distance dependent fluorescence resonance energy transfer (FRET) will be used to evaluate the state of the interaction Sites for incorporating or inserting labels may be selected using x-ray crystallographic data or computer programs. For example, amino acids in an interaction site (e.g. tryptophan) that can be substituted with a fluorescent amino acid analogue (e.g. 7-azatryptophan) may be selected using computer programs. Known databases and multiple sequence alignments may also be used to locate where tryptophan residues may be substituted into interfacial regions for proteins lacking such residues.

Incorporation of Biomolecular Interactions Within a Carrier

Once interacting molecules are selected, the biomolecular interactions are formed and incorporated in a carrier such as silica based glass, organic polymers, organic-inorganic hybrid materials or non-silica based inorganic polymers (e.g. I. Manners. Polymers and the Periodic Table: Recent Developments in Inorganic Polymer Science. *Angew. Chem. Int. Ed. Engl.,* 1996, 35, 1602; and P. Nguyen, P. Gómez-Elipe and I. Manners. Organometallic Polymers with Transition Metals in the Main Chain. *Chem. Rev.,* 1999, 6, 1515). The preferred carrier is a silica based inorganic or hybrid organic-inorganic glass that physically entraps the biomolecular interaction, and is preferably formed by the sol-gel method. The carrier is selected so that it reduces the potential for aggregation of the molecules in the biomolecular interaction upon disruption. In an embodiment, the biomolecular interaction is incorporated by adding the interacting molecules to a solution containing a mixture of water and an alkoxysilane, such as tetraethylorthosilicate (TEOS), which may be alone or mixed with other silanes, including alkyltrialkoxysilanes, dialkydialkoxysilanes, bis-silanes, polyglyeryl silicates, or other silicon or metal-based precursors. This solution is treated with acid and may be sonicated to promote hydrolysis of the silanes. A buffered solution containing the molecules of interest, along with any additives (i.e., polymers, osmolytes, buffers or other species) is then added to the hydrolyzed silane to bring the pH to physiologically acceptable levels (between 4 and 10) and to dilute any ethanol that may be produced as a byproduct of the hydrolysis reaction (to about 20 to 35% if TEOS is used). The resulting mixture is quickly poured into a mold to form a monolith (Ellerby, L. M. et al., Science 1992, 255, 1113), cast into a microtiter well (Alstein M. et al, J. Agric. Food Chem. 1999), or cast as a thin film onto a surface (Aylott, J. W. et al, Chem. Mater., 1997, 9, 2261). Alternatively, the mixture may be formed into an array of spots on a solid surface using pin-spotting, stamping, inkjet deposition or screen printing technologies. For monoliths, the sol rapidly becomes very viscous until it eventually sets, forming a very soft gel. The gel then ages and dries at room temperature for a period of several weeks to form a clear, mesoporous glass matrix which has the molecules incorporated in the cavities of the glass (Dave, B. C. et al, Chem Mater. 1995, 7, 1431).

For films and spots, the aging and drying is greatly accelerated, occurring over a period of as little as 30 minutes (Dave, B. C. et al Chem. Mater. 1995, 7, 1431), and resulting in fundamentally different properties as compared to monoliths (Yan, Y., et al, Chem. Mater. 1995, 7, 1431). In the majority of cases, encapsulated molecules retain substantial biological activity for periods of several months (Miller, J. M., et al Non-Cryst. Solids, 1996, 202, 279).

The aging of the silicate matrix can be manipulated by controlling the type and level of precursors and additives used to for the material, the silicon to water level during hydrolysis and gelation, the amount of water present during aging, the pH and buffer content of the surrounding solution, the presence of surfactants or polymers in the surrounding solution, or the aging temperature. In addition, further chemical modifications can be done to the aging matrix, such as addition of monofunctional silanes (i.e., trimethylethoxysilane, chlorosilane, etc) to cap all silanols and arrest aging. By doing so entrapped proteins can retain significant or almost complete conformational freedom while being prevented from leaching from the matrix. The encapsulated proteins are able to switch between compact and extended (or partially unfolded) conformations as a means of generating an analytical signal that is related to the state of a biomolecular interaction.

Other silicone precursors may be used to prepare a silica-based glass, including those of the type R-Si-$(OEt)_3$, $R_2$-Si-$(OEt)_2$, $(OEt)_3$Si-R-Si-$(OEt)_3$ where R is an alkyl, aryl, or other functional group. Groups other than ethoxy, such as methoxy, choro and silazane. Hydrogenative coupling may also be used for glass formation.

Protein stabilizing materials may be used in the preparation of a sol-gel. The additives include, but are not limited to, polymers such as polyvinyl alcohol (PVA), polyethylene glycol (PEG), polyethylene oxide, polyethylimine and poly (N-vinylimidizole), and polymer-polyelectrolyte mixtures such as lactitol-DEAE dextran. The additives may improve protein stability due to electrostatic interactions and osmotic effects on the protein hydration shell. The large size of these polymers may ensure minimal leaching after entrapment, and such species may be useful in manipulating pore sizes so as to provide sufficient room for proteins to undergo large-scale conformational changes. Other additives can include small molecular weight compounds such as sarcosine, sorbitol, and α-glutamate, which are naturally occurring osmolytes that are known to stabilize polypeptides. The compounds may be used to stabilize a polypeptide during entrapment and they can be removed by incubating in a buffer solution.

The additives listed above may be physically entrapped, or may be covalently attached to the matrix, either by forming appropriate precursors (such as a sorbitol-linked silane) or by covalent attachment of the additives to an appropriately functionalized matrix.

A biomolecular interaction may be incorporated in a sol-gel carrier using the method described by Gill, I. and Ballesteros, A. J. (JACS, 1998, REF). In this method, the sol that is formed by hydrolyzing TEOS is rotary evaporated to remove the ethanol produced in the reaction. A polyol (such as PEG or PVA) or higher order alcohol (ethylene glycol or glycerol) is then condensed onto the resulting sol to form a new precursor with the approximate molecular formula Si(additive)$_2$. Hydrolysis of this precursor produces a non-denaturing polyol that stabilizes proteins. These new precursors may be used to form silica-based materials afforded by rehydrolysis of the precursors under mild aqueous conditions, followed by gelation in the presence of a protein to form a biologically-doped glass. The compatibility of the precursors with proteins may provide improvements in entrapment activity.

A carrier used in the present invention can be in any shape suitable for analysis. For example, it can have the shape of rods, cubes, sieves, powder, or thin films coating conventional glass plates or any other inert solid support. Thus, a method according to the invention can be performed for example by preparing optic fibers, planar supports (waveguides), or slides, coated with doped sol-gel derived glass layers. Such surfaces may also be coated with small spots of sol-gel derived glass to form an array. Formation of the sol-gel derived spots may be done by pin spotting, stamping, inkjet deposition or screen printing. The optic fibers, supports, coated wells of microtiter plates, slides or arrays may be used for clinical, analytical, or industrial purposes.

A biomolecular interaction may be disrupted in the carrier to provide non-complexed molecules of the interaction in the carrier. For example, a protein—protein interaction may be disrupted by heating, changing the pH, treating with a sufficient concentration of urea or guanidine hydrochloride denaturant, or by removal of an activator (i.e. $Ca^{2+}$ in the case of CaM-mellitin complex).

Analysis of Complexes/Components of Complexes

A biomolecular interaction incorporated within a carrier in accordance with the invention may be characterized both in the presence and absence of test compounds, which may be potential inhibitors or stimulators of the biomolecular interaction.

Test compounds include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, $F(ab)_2$, and Fab expression library fragments, and epitope-binding fragments thereof)], and small organic or inorganic molecules. A test compound may be an endogenous physiological compound or it may be a natural or synthetic compound.

A test compound can be a polypeptide or nucleic acid that comprises the biomolecular interaction or region thereof (i.e. modular domain), which has been modified using conventional methods some of which are described herein. The test compound can also comprise a peptide or nucleic acid molecule corresponding to a site of interaction of the molecules in a biomolecular interaction or a mimetic of a polypeptide or region thereof that comprises a biomolecular interaction.

The term "stimulator" refers to a molecule that increases the formation of a biomolecular interaction and thereby may increase the amount of, or prolong the duration of, the activity of a biomolecular interaction or molecules of the interaction in vivo. The term "inhibitor", as used herein, refers to a molecule which decreases the formation of a biomolecular interaction and thereby may decrease the amount of, or shorten the duration of, the activity of a biomolecular interaction or molecules of the interaction in vivo.

The invention contemplates a method for screening a compound to determine the degree of inhibition or stimulation (i.e. binding) of a biomolecular interaction by the compound, or if it interferes with the biomolecular interaction. The method involves contacting a compound to be tested with molecules of a biomolecular interaction incorporated within a carrier as described herein. The molecules are preferably not complexed but are capable of forming a biomolecular interaction in the carrier. Therefore, a method of the invention may initially involve disrupting a biomolecular interaction by applying a denaturant (e.g. temperature, pH, or urea). The denaturation of the interaction may be achieved using a cyclic denaturation (temperature, urea, or pH cycling). The screening method is carried out under conditions suitable for the formation of a biomolecular interaction. The conditions are selected having regard to factors such as the nature of the molecules forming the interaction. In a preferred method of the invention the carrier is a silica based glass, most preferably a sol-gel derived glass. The biomolecular interaction within a carrier is preferably cast on the surface of an optical fiber, planar supports (waveguides), a slide, a microtiter well or an array of sol-gel derived spots formed by pin spotting, stamping, inkjet deposition or screen printing.

In a screening method of the invention, at least one of the molecules forming the biomolecular interaction is labeled intrinsically or extrinsically at the site of an interaction producing a detectable change on formation/disruption of the interaction. Thus, inhibition or stimulation (i.e., binding) by a test compound may cause a change in the amount of a detectable change produced by a label at the site of interaction of the molecules. The method may be a specific color test reaction, NMR or ESR analysis, analysis via emission or absorption, luminescence, fluorescence, phosphorescence tests and/or electrochemical tests depending on the selected label. Preferably, the method uses one or more fluorescence labels and an optical change is detected. Excitation of labels may be done directly or via evanescent wave excitation, or by a combination of both methods. Recapture of fluorescence may also be direct or by evanescent recapture and waveguiding, or a combination of both methods.

Control reaction mixtures without the test compound or with a placebo may also be prepared. The method of the invention may be scaled up to assay a large number of biomolecular interactions against a large number of compounds.

Test compounds may be pre-screened prior to screening in the method of the invention. Pre-screening methods may be based on normal or frontal affinity column chromatography. For example, gravity flow or syringe-pumped glass columns that contain silicates doped either with fluorescent biomolecular interactions or single molecules of the interaction may be used. The column may be interfaced to a fluorimeter, via optical fibers, to determine spectroscopically if various elution gradients (i.e., denaturant gradients) can reversibly disrupt the biomolecular interaction. Alternatively, the column may be interfaced to a mass spectrometer to determine the retention times of compounds or of an indicator ligand of known association constant if a competition-based experiment is done. If a biomolecular interaction is used, a mildly denaturing eluent may be first used to disrupt the interaction. If a single molecule of the interaction is used, the initial eluent can be a buffer. In both cases, a potential inhibitor may be injected onto the column and eluted through as the concentration of denaturant (if used) is decreased, either in a linear or step fashion. As the denaturant concentration is decreased the inhibitor will bind to one of the molecules of the biomolecular interaction and be retained on the column, while non-disrupting compounds elute in the void volume. In one embodiment, a final elution with a more strongly denaturing eluent may be used to remove bound inhibitor from the column, causing it to elute, and this eluent can subsequently be tested (e.g. by mass spectrometry) to identify the structure of any compounds that interacted with the column. Using this approach, non-disrupting compounds within a mixture elute rapidly, and can be discarded as candidates for further testing, while disrupting compounds are retained on the column, and are then further characterized. Therefore, a relatively complex mixture of test compounds can be rapidly and efficiently separated into those that show some level of interaction with the entrapped proteins and those that do not.

Pre-screening methods may also use short columns, such as analytical scale HPLC or FPLC columns or capillary columns, loaded with a sol-gel derived silicate material containing an incorporated biomolecular interaction. This method does not require labeling of the molecules of the biomolecular interaction, providing a more cost effective and efficient pre-screening method.

In an embodiment of the invention, a fluorescence screening method is provided for assaying protein—protein interactions. In the method a protein-doped silicate is dipcast, spin coated, sprayed, pin spotted, stamped, screen printed or deposited by inkjet methods onto the surface of an optical fiber, planar support (waveguide), or a slide, allowing a "remote-sensing" configuration ideally suited to detection of compounds in multi-plate wells. On aging the silicate films, the pore sizes within the matrix are such that the proteins are encapsulated within the glass, while small compounds can penetrate. Intrinsic or extrinsic fluorescence emission of the encapsulated biomolecular interactions may be used to examine the structure, dynamics and stability of the entrapped biomolecular interaction. Fluorescence spectroscopy is ideally suited for this analysis since it provides detailed information about both the internal environment of sol-gel derived matrices during aging and drying, (J. D. Brennan, Appl. Spectrosc. 53 (1999) 106A and references therein; U. Narang, et al, J. Phys. Chem. 98 (1994)8101; F. Nishida et al., J. Amer. Ceram. Soc. 78 (1995) 1640; U. Narang et al. Appl. Spec. 47 (1993) 229; K. Matsui et al, J. Phys. Chem. 93 (1989) 4991); and about the structure (U. Narang et al Anal. Chem. 66 (1994) 3139; S. A. Yamanaka et al J. Am. Chem. Soc. 117 (1995) 9095; T. E. S. Dahms and A. G. Szabo, Biophys. J. 69 (1995) 569; and M. R. Efink, Biophys. J. 66 (1994) 482), dynamics (B. C. Dave et al., Chem Mater. 7 (1995) 1431; R. Wang and F. V. Bright, J. Phys. Chem. 100 (1996) 8580, and J. S. Lundgren and F. V. Bright J. Phys Chem 100 (1996) 8580), activity (Z. Zhang et al Chem Mater. 10 (1998) 3974), and long-term stability (Zhang et a; Anal. Chem. 69 (1997) 3940; and M. R. Efink, Biophys. J. 66 (1994) 482) of both free and entrapped proteins.

Conventional methods may be used to cast the sol-gels on optical fibers. In an embodiment, a commercially available bifurcated fiber adapter may be mounted into the sample compartment of a standard steady-state fluorimeter. The distal end of the fiber bundle can then be optically interfaced to a sol-gel coated fiber or slide, and can transport excitation and emission radiation to and from the sample. This approach is amenable to virtually any excitation/emission wavelength combination, and it can be adapted for use with most steady-state fluorimeters. Therefore, using a few lenses to transport excitation and emission radiation between the fiber bundle and the single coated fiber, a relatively inexpensive instrument can be designed which is adaptable to any standard steady-state fluorimeter.

A multi-well fluorescence plate reader may also be utilized in the invention. Each individual well is coated with a sol-gel derived film containing a particular protein—protein interaction. A series of steps can be performed involving addition of a denaturant, addition of test compound, incubation, dilution with buffer to reduce the denaturant level, followed by fluorescence analysis to determine if the compound is an inhibitor and hence a potential drug candidate.

The fluorescence of the protein—protein interaction in the absence and presence of any compounds is measured through the optical fiber or within the plate-reader. The protein fluorescence indicates whether pair of proteins is in a complex.

In another embodiment, the fiber may be used to excite and collect fluorescence from sol-gel spots on the surface of a solid support. These spots may be formed by pin spotting, stamping, inkjet methods or screen printing. The spots may be nanoliters to microliters in volume and will contain the fluorescent biomolecular interaction. Compounds for testing, denaturants and rinse buffers can be introduce via pipette or by microfluidic delivery systems to manipulate the state of a biomolecular interaction. Individual spots on an array can be read by moving the fiber or the slide to position the fiber over a particular spot. A fiber-optic based steady-state fluorimeter can also be used to analyze an interaction or disrupted interaction contained within the sol-gel derived spot. In particular a fiber-optic based fluorimeter based on a helium-cadmium laser can be used in conjunction with fluorescent probes that absorb at 325 nm or 442 nm i.e., when the interaction is labeled with nitrobenzoxadiazole, acrylodan, a europium chelate or a fluorescence donor-acceptor pair. Such an instrument utilizes a helium-cadmium laser for excitation, a perforated mirror beamsplitter, a single optical fiber for delivery of excitation and return of emission radiation, and a monochromator/PMT assembly for spectral acquisition. This system has the advantage that it can be moved between sol-gel derived spots allowing the assay to proceed more rapidly. The instrument is also amenable to automation if a microtiter well (96 or 384 samples) is used, allowing high throughput. Other instrument formats that may be used include a commercial fluorimeter interfaced to a bifurcated optical fiber bundle or light-emitting diode, which would be interfaced to the fiber.

In a further embodiment, a charge coupled detector (CCD) camera may be used to image the array of sol-gel derived spots containing the biomolecular interactions through a series of filters to measure the fluorescence signals for individual spots simultaneously. Standard image processing methods will be used to analyze the images and quantify inhibition.

Polypeptides that have a single tryptophan (Trp) residue, a single 7-azatryptophan residue, and/or a second site (usually a free Cys) which can be exclusively labeled with a second fluorophore, provide a unique opportunity to examine both local structure, via normal or polarized emission of single probes, and global structure via resonance energy transfer experiments. The emission characteristics of the polypeptides are sensitive to temperature and denaturant concentration, allowing monitoring of the structure, dynamics and stability of entrapped proteins under different conditions. Using this approach the fluorescence responses of entrapped proteins to alterations in their local environment, such as a change in pH, viscosity or concentration of analyte (i.e., drug candidate), can be examined.

In an embodiment, after the fluorescence of the protein—protein interaction is determined and/or analyzed in the absence of a test substance, the interaction incorporated within the sol-gel derived glass may be heated, subjected to a pH change or incubated in a solution of urea or guanidine hydrochloride denaturant of sufficient concentration to disrupt the interaction, and the fluorescence of the disrupted system measured and/or characterized. Any disruption will cause the label at the protein-interface to have a significantly altered fluorescence signal compared to the previous measurement. The disrupted interaction incorporated within the sol-gel interacted with a small volume of a test compound (or a mixture of compounds from a combinatorial library) for screening. The simultaneous dilution of the denaturant remaining in the sol-gel glass (or the drop in temperature or shift in pH) will be sufficient to cause the protein—protein interacting system to reform in the sol-gel matrix, thus recovering the original intense fluorescence signal of the label if no disruption of the complex occurs (i.e., the test compound is not a drug candidate). If the original fluorescence is not recovered then the test compound or mixture of compounds has disrupted the protein—protein interaction, and it can be tested as a drug candidate.

Samples can be excited on optical fibers at wavelengths in the range from 190 nm to 1100 nm. A lamp, light emitting diode or laser source can be used. Laser sources are preferable due to the high intensity, monochromaticity and collimated nature of such sources. Laser sources can be made tunable by using a pulsed pump laser to excite a dye within a second laser, producing a pulsed dye laser output, which can be tuned across the emission spectrum of the dye. The pulsed output can then be put through a frequency doubling crystal to produce tunable laser emission in the ultraviolet region, which is where both native and 7-aza-tryptophan incorporated proteins absorb.

An economical platform suitable for a method of the invention uses a nitrogen laser with an output of 337 nm as the pump laser, a dye laser module where, as one example, rhodamine 6G is used to produce tunable output between 540 nm and 640 nm, and a second harmonic generator unit (frequency doubler) is used to produce UV output between 280 nm and 320 nm, spanning the range for excitation of tyrosine, tryptophan and 7-azatryptophan. Using such an excitation source, tryptophan can be exclusively excited in the presence of tyrosine using excitation at 295 nm, or 7AW can be exclusively excited in the presence of Trp using excitation at 315 nm. Such tunability is not easily achievable for fiber optic systems with any other type of excitation source (such as a Xe lamp or LED and monochromator). However, such sources can be used in the present invention using a bifurcated optical fiber interfaced to a well, single fiber, or another sol gel derived device, or if a sol-gel derived array of spots is used.

The use of a pulsed laser source requires specialized detection apparatus when steady-state measurements are to be made through optical fibers. The detection system for steady-state experiments may consist of a gated integrator/boxcar averager combination for signal acquisition, with a monochromator and fast-rise photomultiplier tube for detection of the signal. Using these components, both excitation and emission spectra can be obtained, or steady-state intensity or anisotropy can be monitored at any excitation/emission wavelength combination, making for a very powerful instrument for characterizing the behaviour of proteins entrapped in sol-gel films on optical fibers.

In another embodiment, the instrument could be configured to measure time-resolved fluorescence by the stroboscopic method (REF). Both organic or lanthanide-based fluorescence energy donors could be used in conjunction with organic fluorescence energy acceptors, and the emission decay profile of the donor and/or acceptor measured to evaluate the state of a biomolecular interaction using FRET methods.

By collecting decays at several emission wavelengths the decay associated spectra (DAS) and time-resolved emission spectra of the encapsulated molecules can be elucidated. For proteins, DAS can be used to predict the local secondary structure of proteins in the region of the Trp residue. In the case of 7-azatryptophan, DAS can be used to quantitate how much probe is solvent exposed in the population. The ability to measure fluorescence lifetimes allows examination of the structure of encapsulated proteins at very sensitive levels. In addition, time-resolved anisotropy decay measurements allow examination of the local and global dynamics of encapsulated proteins, and thus enable determination of the mobility of species inside the pores of the glass.

A detection system that is capable of collecting fluorescence decay profiles on the picosecond to nanosecond time-scale is preferably used to measure time-resolved fluorescence parameters. An appropriate time-resolved detection system for use with a nitrogen laser based excitation system is the stroboscopic system manufactured in Canada by Photon Technologies International.

In another embodiment, a fiber-optic based steady-state fluorimeter can also be used to analyze an interaction or disrupted interaction. In particular a fiber-optic based fluorimeter based on a helium-cadmium laser can be used in conjunction with fluorescent probes that absorb at 325 nm or 442 nm i.e., when the interaction is labeled with nitrobenzoxadiazole, acrylodan or a europium chelate. Such an instrument utilizes a helium-cadmium laser for excitation, a perforated mirror beamsplitter, a single optical fiber for delivery of excitation and return of emission radiation, and a monochromator/PMT assembly for spectral acquisition. This system has the advantage that it can be moved between solutions allowing the assay to proceed more rapidly. The instrument is also amenable to automation if a microtiter well (96 or 384 samples) is used, allowing high throughput. Other instrument formats that may be used include a commercial fluorimeter interfaced to a bifurcated optical fiber bundle or light-emitting diode, which would be interfaced to the fiber.

Applications of the Sol-Gels and Methods of the Invention

The methods according to the invention can be applied to detect and analyze biomolecular interactions in biological samples, tissues, cells, cell extracts and it can be applied to qualitative and/or quantitative analysis of biomolecular interactions.

Medical diagnostics is another application of the present invention. For example, small organic molecules, inorganic ions, and other substances which modulate a biomolecular interaction may be detected in biological samples.

Compounds that stimulate or inhibit these biomolecular interactions and have valuable pharmacological properties will be identified using the methods of the invention. For example, two targets for new antibiotic development in which the target compound activity is based on the disruption of native protein-dimer interface have been identified. The first is tryptophanyl-tRNA synthetase (TrpRS) from *B. subtilis* which has a naturally occurring Trp residue (Trp 92) located at the dimer interface. Work with TrpRS will be extended to include fluorescently-labelled single Cys mutants. Since the protein is a homodimer, both monomers will end up being labelled with the same probe, potentially negating the use of FRET-based signals. In this case, NBD may be used as the label since it is known to undergo concentration and distance dependent self-quenching,[8] which should provide a useful signal in response to homodimer-monomer equilibria.

The second system is HIV integrase, which has multiple Trp residues, one of which is at the dimer interface. This protein will also be prepared as a single Cys mutant for labelling. This protein is an integral part of the mechanism of HIV infection, and thus any drug leads that are identified by the assay will likely be of interest to potential partners in the pharmaceutical industry. TrpRS and molecules interacting with TrpRS, and HIV integrase and molecules interacting with HIV integrase can be incorporated within a carrier in accordance with the invention. Compounds that inhibit these interactions can be valuable as antiviral, antibacterial, or antifungal compounds.

The sterile-alpha-motif (SAM) domain may be incorporated in a carrier in accordance with the present invention. The domain is present as a conserved module in a number of signaling proteins including tyrosine and serine/threonine protein kinases, cytoplasmic scaffolding and adapter proteins, regulators of lipid metabolism, the GTPases, as well as members of the ETS family of transcription factors. The SAM domain acts as a protein interaction module through the ability to homo- and hetero-oligomerize with other proteins that contain SAM domains. This functional property has been reported to elicit the oncogenic activation of chimeric proteins arising from translocation of the SAM domain within proteins (Jousset, C. et al, Embo J. 1997, 16, 69). The unique aspect of the SAM domain is that it has recently been shown to have a single Trp residue present at the dimer interface (Stapleton, D. et al, Nature). Hence protein—protein interactions involving homo-dimerization of two domains should elicit a large fluorescence response. In addition, several single Cys mutants are available which can be labeled with fluorescent probes that absorb in the visible region of the spectrum, allowing the use of numerous inexpensive light sources, such as light-emitting diodes, in the methods of the invention. In view of the role SAM domains play in various protein signaling events, including axon guidance, cell migration, patterning of the nervous system, and angiogenesis, a biomolecular interaction comprising a SAM domain will provide useful means to screen for drugs such as anti-cancer drugs.

In addition to these dimer-interface interfering protein systems, many other proteins may also be used, based on their usefulness as drug targets. A wide variety of protein-interaction reagents involved in critical pathways associated with the onset of cancer, and a new class of proteins associated with interactions which down-regulate signaling through the ubiquitin mediated target-specific destruction pathway are also suitable for the methods of the invention. Another interaction that can be advantageously studied is the SAP:SLAM complex, which is an important target for human X-linked lymphoproliferative (XLP) disease. SAP is almost exclusively made up of a single SH2 domain, and binds phosphorylated and unphosphorylated peptides derived from SLAM. Given the widespread occurrence of SH2 domains in protein—protein interactions, the engineering of an appropriately labelled SH2 domain should lead to a useful monomer that can be used in a variety of different assays.

Other systems that can be studied include the Polo-box system and the GRF-2:CaM interaction. The polo-box motif involves a homodimeric protein that must be intact to be functional. This protein is of importance in cell cycle control and proliferation, and can control cytokinetic events in cells. The GRF-2:CaM interaction is of importance in the RAS signalling pathway, and hence has potential applications for cancer treatment. In addition to the systems outlined above, a series of other PP interactions will be examined as they are identified by collaborators.

The following non-limiting examples are illustrative of the present invention:

EXAMPLES

Examples 1–3

Fluorescence Response to Complex Formation

Two different sources of calmodulin have been used in the examples, bovine brain calmodulin (BCaM) and spinach calmodulin (SCaM). BCaM was used in the majority of the work owing to commercial availability. However, SCaM has an important property that BCaM does not: it has a single free cysteine residue, which permits site-selective fluorescent labelling, allowing us to extend into energy-transfer based measurements. Numerous literature reports have shown that the two proteins are effectively identical in structure and function. This was confirmed by a series of parallel experiments using the two proteins, including $Ca^{2+}$ and melittin titrations. In all cases, identical data was obtained.

Example 1

BCaM:melittin Complex

The BCaM has no native tryptophan residues, and hence is spectroscopically silent above an absorbance wavelength of 292 nm. Melittin has a single tryptophan residue, allowing selective excitation of the peptide at 295 nm, and it was therefore possible to use fluorescence to follow the state of complexation between CaM and melittin.

Figure 2:
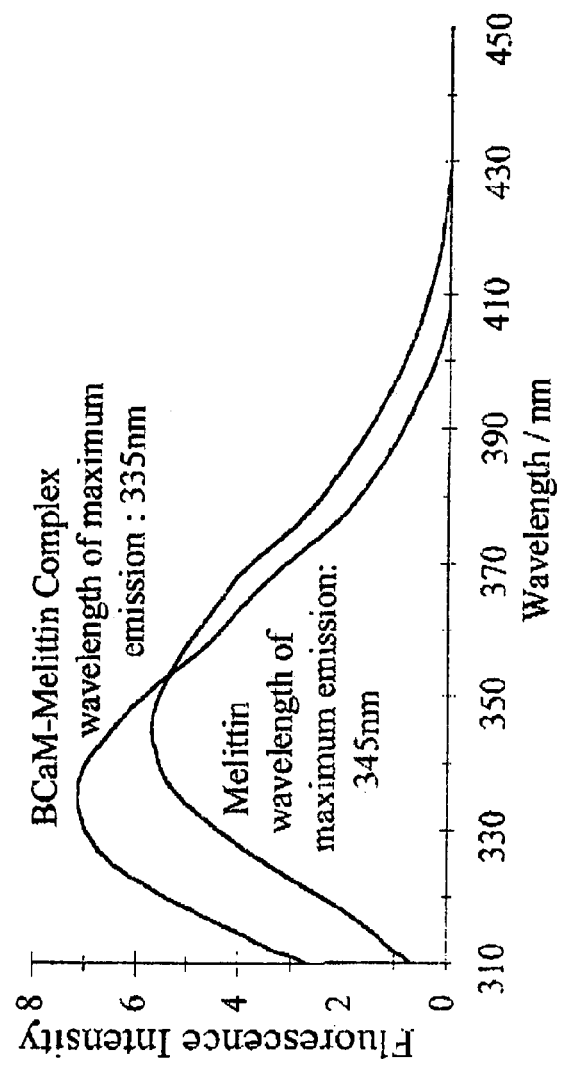
FIG. 2 is a graph illustrating the fluorescence emission spectrum obtained form melittin alone and when complexed with holo-BCaM to produce a BCaM-Melittin interaction complex.
Figure 3:
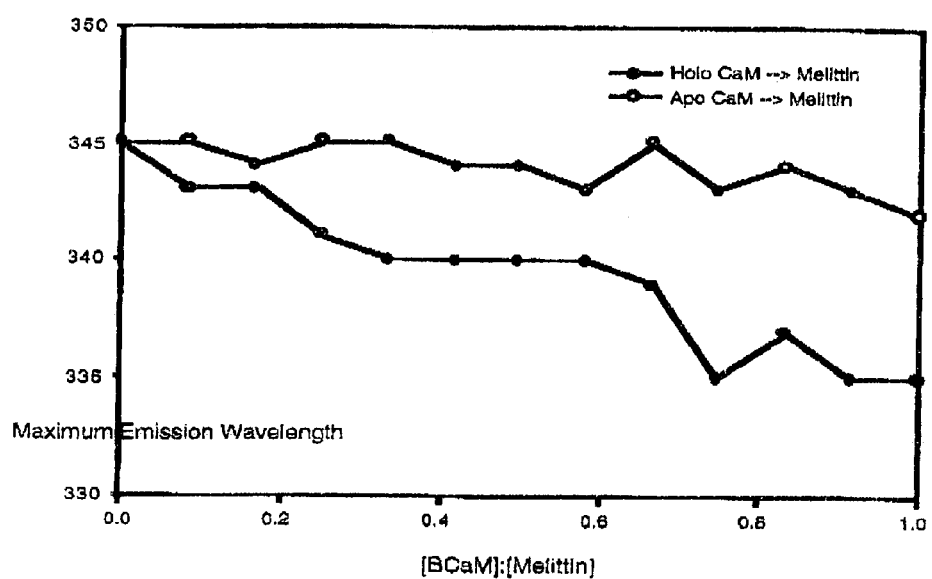
FIG. 3 is a graph illustrating the emission wavelength response of melittin upon complexation with apo and holo BcaM, showing binding only occurs to the holo form.
Figure 4:
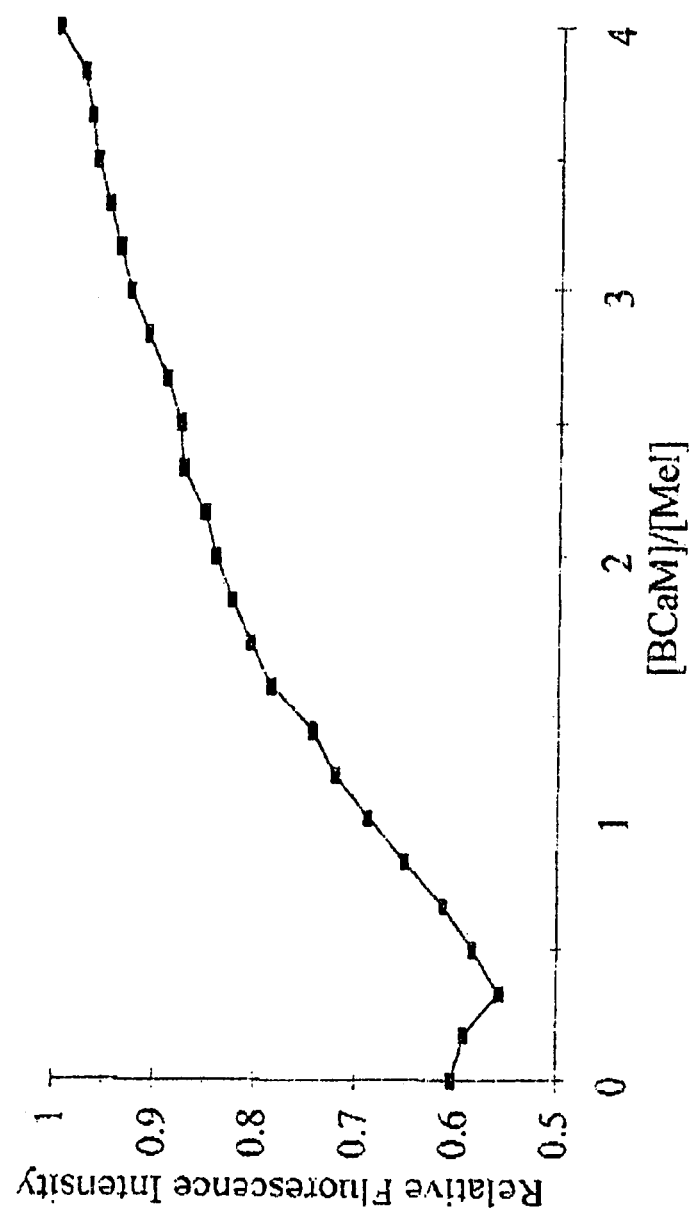
FIG. 4 is a graph of a binding curve for the addition of BCaM to melittin.
Figure 5:
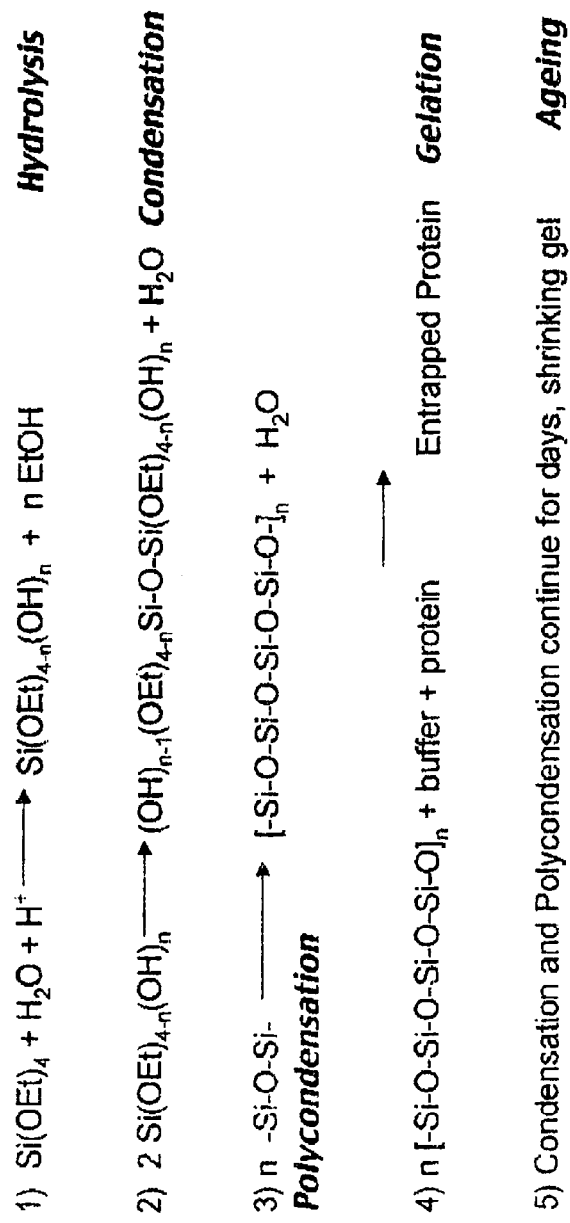
FIG. 5 illustrates a schematic representation of one embodiment of a sol-gel process according to the present invention.

The first trials involved the addition of CaM into melittin until a 1:1 complex was formed. It was shown that a significant increase in emission intensity, and a blue shift in emission wavelength occurred for the Trp residue of melittin upon introduction of holo (calcium-loaded) CaM. Such as response was not observed for apo ($Ca^{2+}$-free) CaM, consistent with expected behaviour. The results of the intensity and wavelength shifts are summarized in FIGS. 2 and 3, and clearly show that the Trp fluorescence of melittin is sensitive to the formation of a complex between BCaM and melittin.

Example 2

Entrapment of an Intact Complex

Once it was determined that Trp fluorescence could follow the state of complexation, we examined the ability to entrap the intact complex into glass. Entrapment studies used the silane precursor tetraethylorthosilicate (TEOS), with a buffer containing the BcaM:melittin complex being mixed in a 1:1 volume ratio with hydrolyzed TEOS to promote gelation. The samples were generally aged for between 10 and 15 days, and resulted in optically clear, durable glasses. Such samples showed no leaching of either component after 7 days of aging (note: (MW of melittin=2840, MW of CaM=16800).

Figure 6:
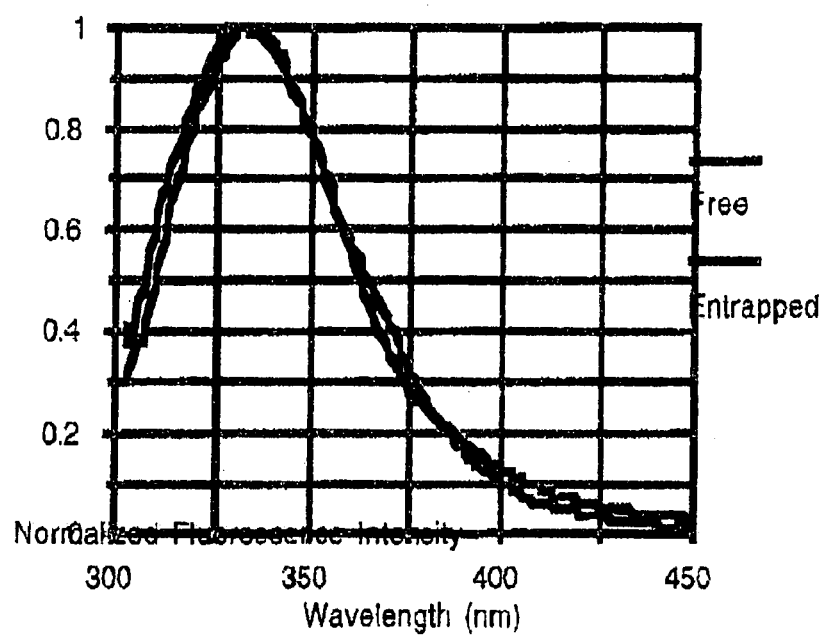
FIG. 6 is a graph illustrating the emission spectra of the holo-BCaM-Mel complex in solution in comparison with the same complex in a sol-gel derived glass according to the present invention.

FIG. 6 shows the emission spectra of the complex in solution as compared to that in glass. The emission maximum of the Trp of melittin at 335 nm is indicative of the complex. Entrapment of melittin alone resulted in an emission wavelength of 345 nm, similar to the wavelength found in solution. Hence, it was determined that the complex was able to withstand the entrapment conditions, which included momentary exposure to low pH and high ethanol concentrations.

Example 3

Reversible Disruption and Reformation of a Complex

It is useful to be able to reversibly disrupt and reform a complex without major changes in the fluorescent signal. Thermal, urea and GdHCl denaturation of the BCaM-Mel complex was examined, both in solution and for the complex entrapped in glass, to determine if the complex could be reversibly separated and reformed. GdHCl gave the most reproducible results, and the highest degree of reversibility. The denaturation curves are shown in FIG. 7.

The data indicate that it is possible to disrupt the complex, even when in a glass matrix. FIGS. 8A and B show the emission wavelength (FIG. 8A) and anisotropy (FIG. 8B) changes for the complex when entrapped in glass, indicating that these signals are quite responsive to the state of the complex. Hence, it is possible to use a combination of intensity, emission wavelength and anisotropy to determine the exact state of the protein complex.

Comparing the unfolding curves using the different fluorescent signals, it is apparent that there is a significant drop in intensity, a red-shift of the spectrum, and a decrease in rotational anisotropy (i.e., an increase in rotational mobility) upon disruption. These signals are consistent with the Trp residue of melittin becoming more solvent exposed, as would be expected if it is no longer bound to calmodulin.

The reversibility of the disruption was evaluated by rinsing the glass with buffer several times, and then recollecting the fluorescence spectrum and anisotropy data. Both the wavelength and anisotropy were reversible upon GdHCl removal, while the intensity recovered to a value that was slightly higher than had been observed originally. The data is given in Table 1.

The slight blue shift and increase in intensity for the recovered complex compared to the original complex may be due to small changes in the level of $Ca^{2+}$ present in the glass after reformation of the complex. The level of $Ca^{2+}$ was shown to have a minor effect on the spectroscopic properties of the complex, both in solution and in glass. It should be noted that this experiment could not be done accurately in solution owing to problems with dialysis of GdHCl. Hence, emission spectra that were obtained after several rounds of dialysis showed only ~15% recovery of signal (possibly due to leakage of melittin through the dialysis tubing), and a final emission wavelength of 340 nm and anisotropy of 0.113. Hence, preferably, the entrapment of the complex into glass is a step to be taken to ensure accurate recovery of the original spectroscopic properties of the complex after disruption.

Examples 4 and 5

Inhibitor Disruption of Reformation of Complex

Example 4

Solution Studies

Once it was determined that reversible denaturation of the entrapped complex was possible, we examined the ability of a known inhibitor of the complex, trifluoperazine (TFP), to disrupt the complex. Control experiments involved an examination of the interactions of TFP with the intact complex, melittin, BCaM, and non-functional complex, obtained using apo BCaM. Interaction of TFP with apo or holo calmodulin alone resulted in no changes in spectroscopic properties. The interaction of TFP with melittin and with the intact BCaM:melittin complex are shown in FIGS. 10A and 10B. Note that no wavelength changes occurred during this titration (not shown).

The results showed that the TFP interacted with the melittin or with the intact complex, resulting in a large decrease in intensity. Similar results were obtained for the disrupted complex. This change in signal was the result of association between the TFP and melittin, which caused energy transfer from melittin to TFP. Examination of the TFP emission (centered at 400 nm) showed an enhancement in intensity as melittin was added, confirming that energy transfer was taking place. Hence, in this particular system the intensity of the signal was not useful for further development of the assay since the TFP affects the signal from the intact complex. For this reason, other fluorescence signals were examined. It was determined that the emission wavelength and anisotropy of the intact complex, or of melittin itself, were not affected by the presence of TFP. This is evident from FIG. 10A, which shows the emission wavelength remaining constant as TFP is added to melittin. Hence these signals were utilized for studies of TFP interactions with the entrapped complex.

Example 5

Entrapped BCaM-Melittin

Described is a complete assay cycle using entrapped BCaM:melittin complex. Based on the results reported in the examples for denaturation of entrapped BCaM:melittin, it was decided that the complex would be disrupted using 1 M GdHCl.

Two trials were done:

1. Addition of 1 M GdHCl, addition of 100 ml of buffer containing no TFP, removal of GdHCl by multiple exchange of the surrounding buffer solution.

2. Addition of 1 M GdHCl, addition of 100 ml of buffer containing sufficient TFP to get a 4:1 ratio of TFP:complex, removal of GdHCl by multiple exchange of the surrounding buffer solution.

Figure 9:
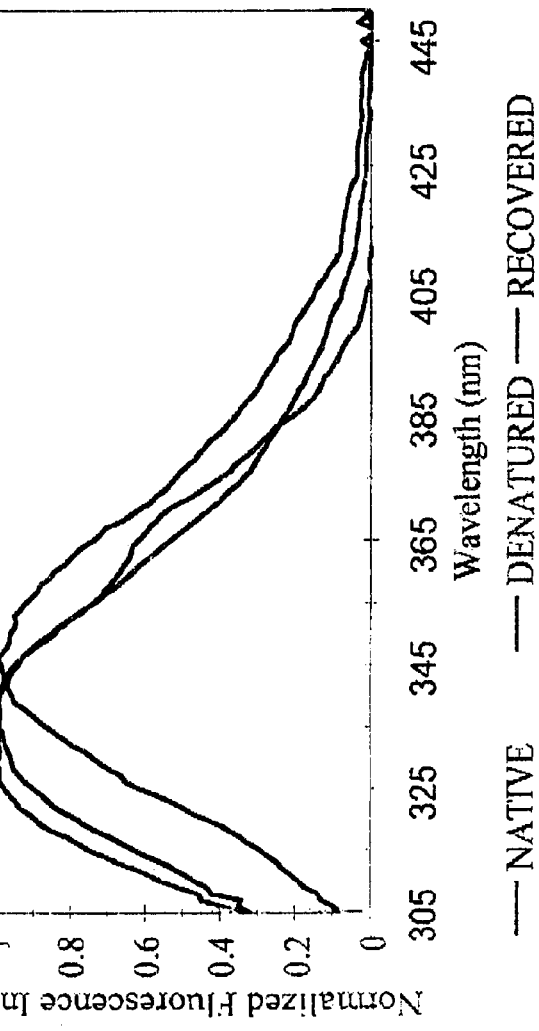
FIG. 9 is a graph illustrating the spectra of native, denatured and recovered BCam-Mel complex in a glass.
Figure 11:
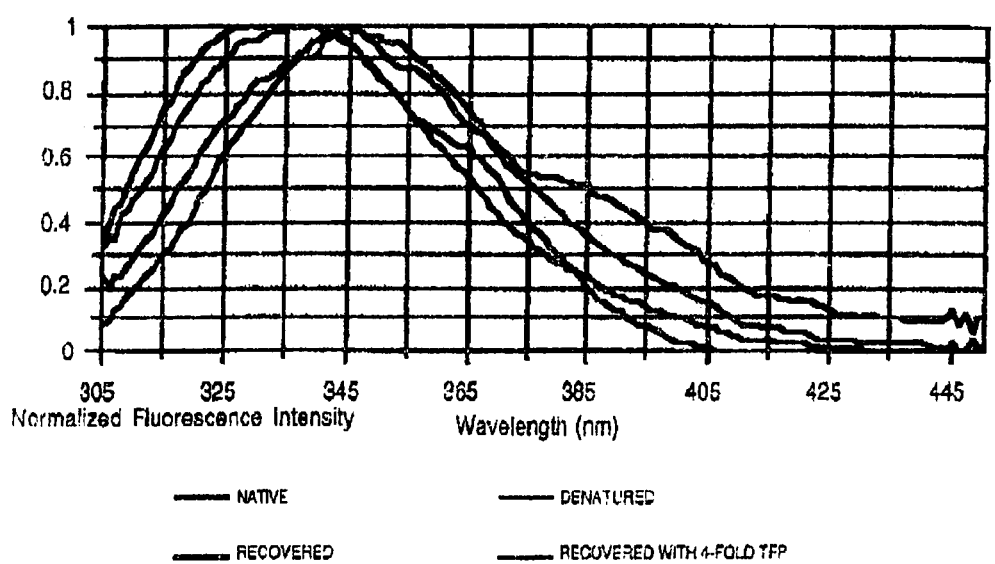
FIG. 11 illustrates the spectra obtained for a complete assay cycle, showing the effects of TFP on recovery of spectral properties of entrapped BCaM-Melittin complex when recovered from GdHCl denaturation in the absence of TFP and presence of TFP.
Figure 13:
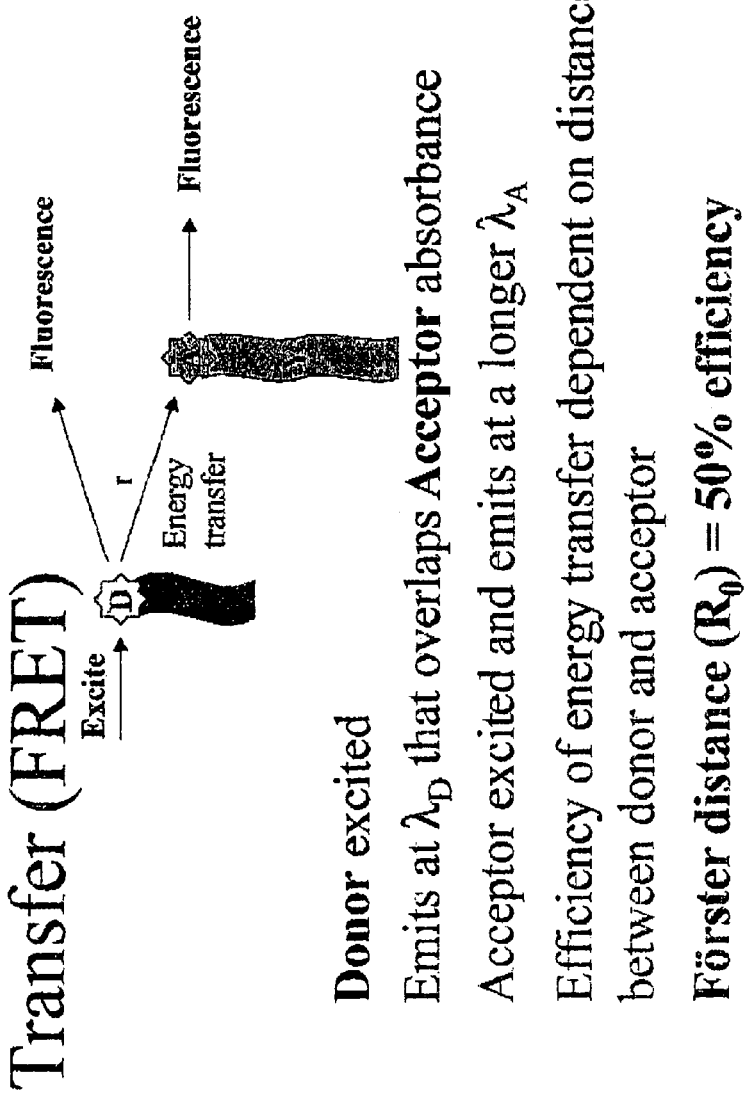
FIG. 13 illustrates the principles of FRET as applied to the present invention.

FIG. 11 shows the results obtained from emission spectral analysis. The spectra have been normalized to allow easier visualization of the emission wavelength data. FIG. 9 shows the reversibility of denaturation for an entrapped protein.

As shown in FIGS. 11 and 12, the BCaM-Mel complex is not able to reform in the presence of TFP. FIG. 11 illustrates the spectra obtained for a complete assay cycle, showing the effects of TFP on recovery of spectral properties of entrapped BCaM-Melittin complex when recovered from GdHCl denaturation in the absence of TFP (spectrum shifts back to native-like properties) and presence of TFP (spectrum retains denatured-like properties). The wavelength is not able to shift from 346 nm, when it should be at 330–335 nm as shown for the complex that was recovered without TFP added. The emission wavelength and anisotropy data for the complex under different conditions are shown in Table 2.

Hence, it is evident that the addition of TFP does disrupt the complex, since the emission wavelength and to a lesser extent the anisotropy both fail to recover to their initial values when TFP is present.

Example 6

Spinach CaM:melittin System

Figure 16:
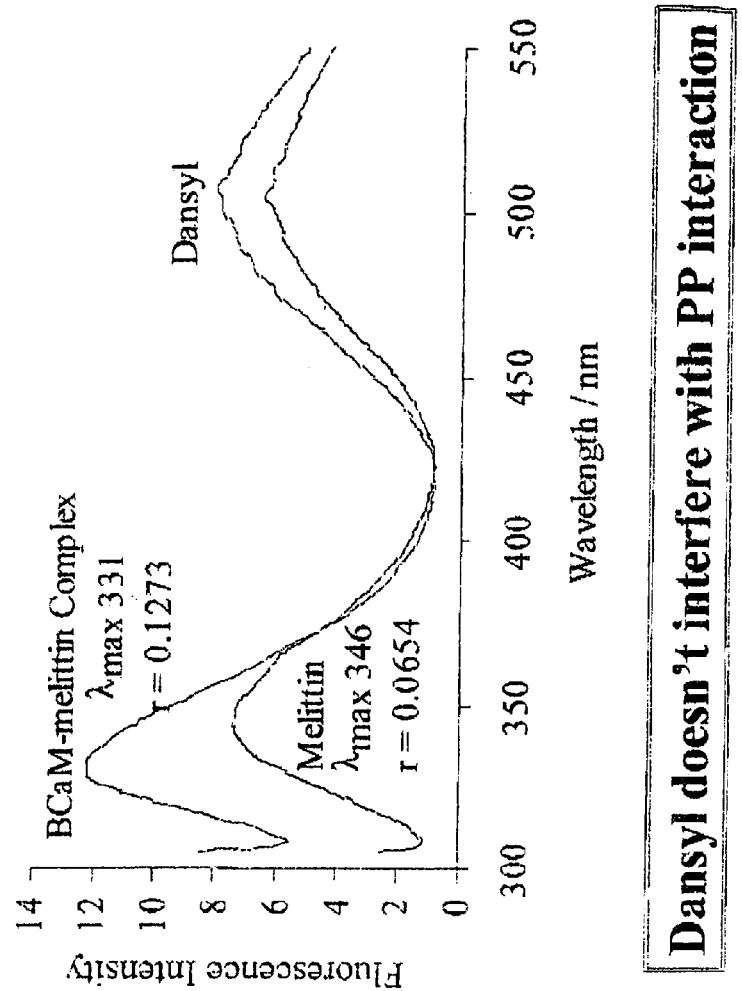
FIG. 16 is a graph illustrating the fluorescence signal from BCaM/Dansyl-Melittin system when excited at 295 nm.

Spinach CaM allows for label of the single cysteine residue with fluorescence probes so that energy transfer mechanisms can be employed to determine distance relationships between the melittin and CaM. Preferably melittin is labelled with a donor, such as dansyl, while CaM will be labelled with an acceptor, such as acrylodan or NBD. By shifting the excitation wavelength from 295 nm (as was used above) to 335 nm (for dansyl excitation), we should avoid interferences with TFP. Other donor-acceptor pairs may also be evaluated. This system may also allow more full exploration of the utility of energy transfer as a potential signal for the development of high-throughput screening. FIG. 16 is a graph illustrating the fluorescence signal from BCaM/Dansyl-Melittin system when excited at 295 nm, indicating both Trp fluorescence and dansyl emission changes upon complex formation.

Example 7

Other Protein—Protein Interaction Systems

Tryptophanyl-tRNA synthetase, both with tryptophan and 7-azatryptophan present at the dimer interface represents another potential system, as well as HIV-integrase.

Example 8

Other Entrapment Protocols

The fluorescently-labelled protein complexes may be entrapped into a variety of different sol-gel derived materials as an initial step for extending the assay to a high throughput format. Presently, BCaM:Melittin and polo-box have been successfully entrapped into PEG-doped TEOS materials and into polyglycerylsilicate-derived materials, both with and without added bis-silane species. In all cases, intact complexes may be entrapped and reversibly denatured using GdHCl. A number of different sol-gel precursors and polymerization routes may be available including the use of osmolyte and PEG doped glasses, to improve the stability of the complex during entrapment, and the use of a hybrid hydrogel/sol-gel method. Also within the scope of the present invention is pin spotting, stamping, inkjet deposition or screen printing of these materials as an initial step toward preparation of arrays.

Examples 9–14

Protein—Protein Interactions

As described in more detail in the following examples, the data show that certain labels may provide better spectroscopic signatures for evaluating protein—protein complex formation, and that alternative methods for forming glasses may improve the stability of entrapped proteins.

Studies on a calmodulin-melittin model system assess the suitability of fluorescently labelled proteins and alliterative fluorescence signals (i.e., energy transfer, fluorescence lifetimes) for development of protein—protein interaction assays.

Example 9

Bovine Calmodulin-Melittin System

Figure 17:
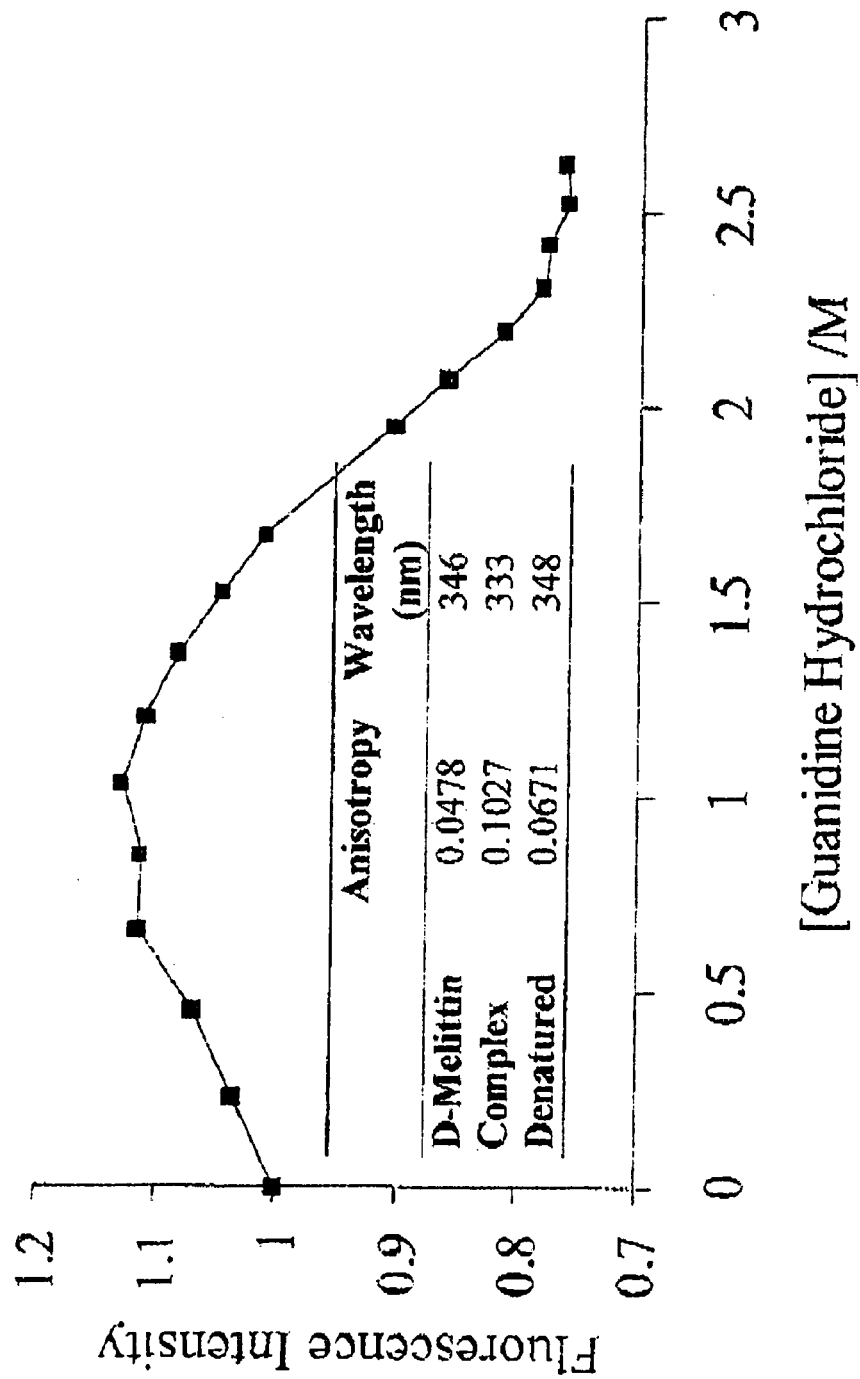
FIG. 17 is a graph illustrating the fluorescence intensity changes with increasing concentrations of guanidine hydrochloride on a BCaM/Dansyl-melittin complex in solution.

The N terminus of melittin can be labelled with a dansyl group, thus allowing for a study of the utility of internal energy transfer from the tryptophan residue of melittin to the dansyl label. This then allows changes in acceptor-donor distance within melittin to be monitored as proof of complexation with calmodulin. Melittin has been labelled to 70% efficiency with dansyl chloride using pH manipulation to prevent other amino groups (i.e., lysine) within the structure from being additionally labelled. FIG. 17 illustrates the fluorescence intensity changes with increasing concentrations of guanidine hydrochloride on a BCaM/Dansyl-melittin complex in solution. Tryptophan anisotropy and wavelength data confirm that the dansyl label does not perturb the interaction.

Figure 18:
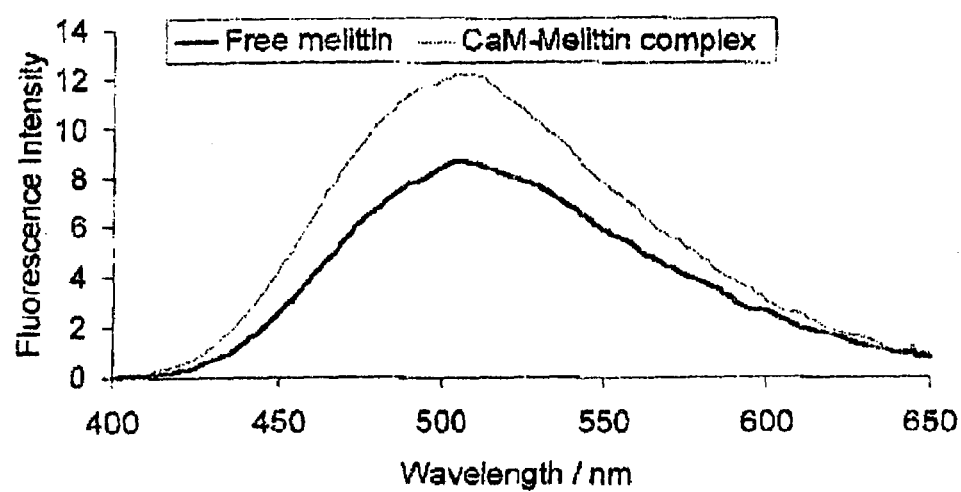
FIG. 18 is a graph illustrating the fluorescence signal of free and complexed dansyl-melittin excited at 350 nm.

Determination of a biomolecular interaction and a spectroscopic response to the interaction is achieved by titration of bovine calmodulin (BCaM) into solutions of the dansyl-labelled melittin. Comparison of the spectra for the free and complexed dansyl-melittin show an increase in the fluorescence intensity of the dansyl label (excited at 370 nm) on binding to calmodulin, as shown in the spectra in FIG. 18.

Monitoring tryptophan fluorescence by excitation at 285 nm also demonstrates an increase in the fluorescence intensity and a blue shift in the maximum emission wavelength. This trend was previously observed in the titration of Cam and non-labelled melittin, indicating that the presence of the dansyl label does not interfere with the formation of the complex.

In the present work, the energy donor has been the tryptophan residue in the melittin, however, while exciting this at 295 nm, the dansyl label is also being excited, preventing calculation of the distance change between donor and acceptor upon the binding of melittin to calmodulin. This problem may be overcome when spinach calmodulin is used, since the single cysteine residue can be labelled with a probe whose absorbance spectrum is separate from that of dansyl. An alternative approach may be where SCaM is labelled with an energy acceptor and dansyl becomes the energy donor.

Example 10

Fluorescence Lifetime Measurements

Figure 19:
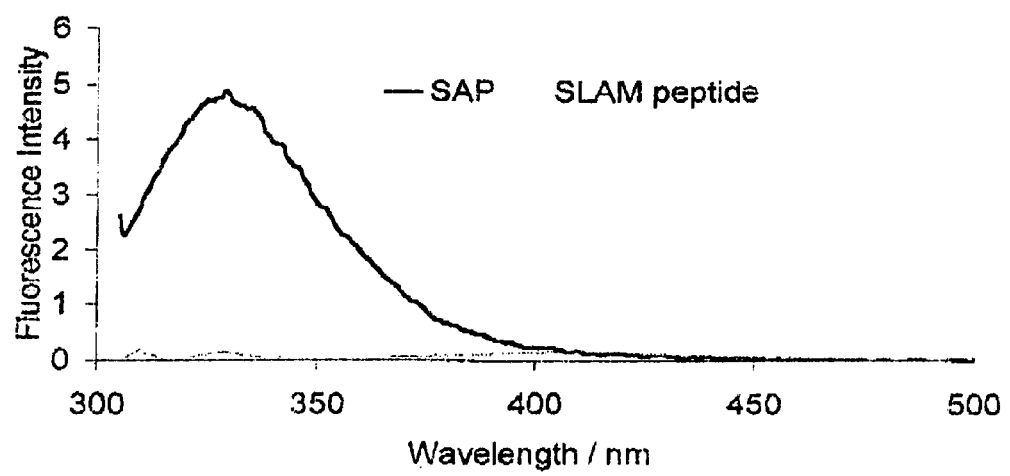
FIG. 19 is a graph illustrating the fluorescence spectra of SAP and phosphorylated SLAM peptide.

The CaM:Melittin system may be used for the study of fluorescence lifetime measurements to better understand the nature of the fluorescence intensity changes resulting from formation of the protein—protein complex. Data has been collected from both free and entrapped BCaM:Melittin complexes. Data from the entrapped system is shown in Table 3. This data shows that the fluorescence decay times change significantly upon disruption of the complex (by addition of 1 M GdHCl), dropping from 29 ns for the complex to 9 ns for the free Dansyl-melittin. Addition of TFP to the disrupted complex followed by removal of GdHCl results in the lifetimes remaining similar to Dansyl-melittin, indicating that lifetimes can follow the inhibition of complex formation. Recovery in the absence of TFP produces the long lifetime (ca 29 ns), demonstrating that the disrupted complex can be recovered in the glass. FIG. 19 is a table showing fluorescence lifetime data for BCaM-Mel in a glass during a complete assay cycle, confirming that TFP disrupts the interaction and that lifetime data can be used to follow the event.

Example 11

SAP-SLAM Interactions

SAP (SLAM Associated Protein) is a small (128 amino acid) protein consisting essentially of an SH2 domain flanked by a 5 residue amino terminus and an unstructured 26-residue carboxy terminus. SAP has been found to bind to the cytoplasmic tail of SLAM (also known as CDw 150), a transmembrane protein located on the surface of B and T cells which plays a key role in the regulation of B cell proliferation. SAP has been found to interact with a specific site flanking Tyr-281 of SLAM (Signaling Lymphocytic Activation Molecule), thereby inhibiting the binding of other SH2 proteins, such as SHP2 tyrosine phosphatase. However, in contrast to other SH2 domains, the phosphorylation of the tyrosine residue is not essential for stable binding.

Figure 20:
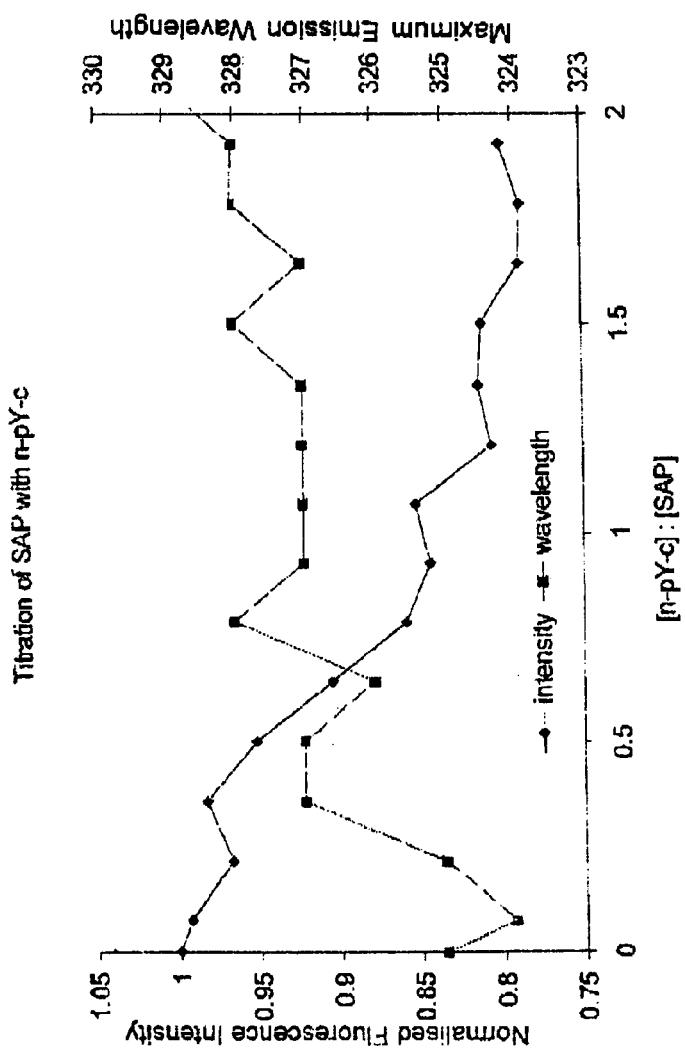
FIG. 20 is a graph illustrating the effects of titration of SAP with n-pY-c on fluorescence intensity of SAP.
Figure 22:
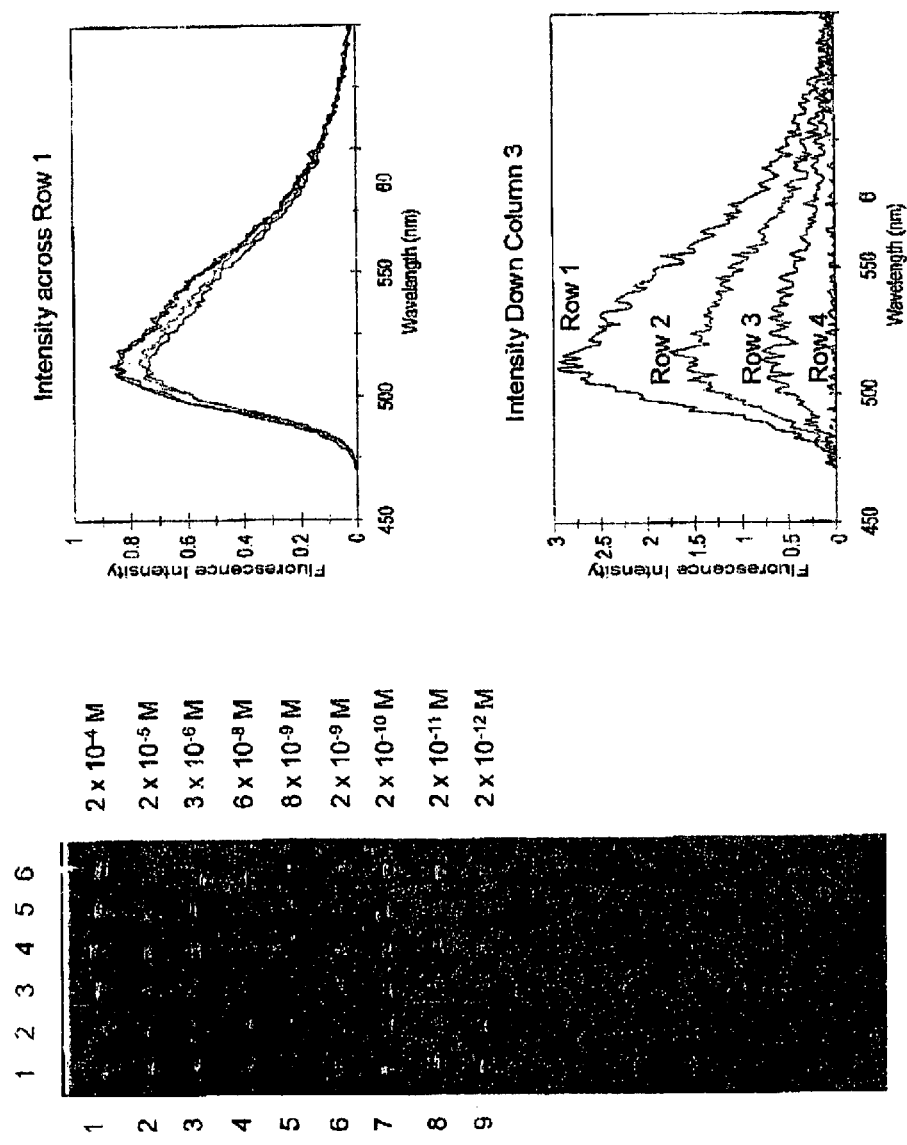
FIG. 22 is an array of sol-gel derived silica spots containing an entrapped protein (fluorescein labelled human serum albumin) on a glass slide and spectra obtained from the fiber optic fluorimeter shown in FIG. 21.

In order to investigate SAP-SLAM binding, small SLAM peptides corresponding to residues 276–286 of SLAM, containing either a phosphorylated or non-phosphorylated tyrosine residue at position 7 have been synthesized. These peptide-SAP complexes have been shown to have dissociation constants in the region of 150 nm and 330 nm respectively. As SAP contains a single tryptophan residue at position 64 within the SH2 domain it lends itself to monitoring by fluorescence techniques. Although the peptides also contain a spectroscopically active tyrosine, it is possible to selectively excite the tryptophan above 292 nm, as shown in the spectra in FIG. 20 (SAP and SLAM proteins at equal concentrations).

Experiments were conducted in which the phosphorylated SLAM peptide (n-pY-c) was titrated into a SAP solution and the complexation monitored by following changes in the tryptophan emission of SAP. As may be seen in FIG. 21, it was found that there was approximately a 20% decrease in the intensity of the tryptophan emission of SAP upon reaching a peptide: SAP ratio in the region of 1:1 (actual [n-pY-c]: [SAP]=1.2), with a slight red shift in the maximum emission wavelength.

This preliminary result indicates the binding of the peptide results in a conformational change in the SAP that produces a greater exposure of Trp to solvent. Overall, the results indicate that monitoring of changes in Trp fluorescence is a suitable method to follow the protein—protein interaction.

Example 12

Improved Fluorescence

A combination of approaches are available to improve labelling: First, fluorescein-labelled peptides can be prepared which can be used for eventual energy transfer experiments wherein SAP is labelled with either an energy donor or acceptor. Second, as the expression system is available for the SAP protein it is also possible to replace the tryptophan residue with 7-azatryptophan and so obtain an enhanced fluorescence signal which should be more sensitive to the protein—protein interaction.

The SAP-SLAM complex may be reversibly disrupted, preferably using both thermal and chemical denaturation methods (for example pH, GdHCl and Urea). Both fluorescence and electrophoretic (native PAGE) methods may be used to demonstrate that disruption of the complex has been achieved and to investigate the reversibility of the process, the latter being key to the suitability of the method for drug screening.

Once solution characterization is complete, an entrapment protocol for the SAP-SLAM complex may be developed. The SLAM peptides are slightly hydrophobic and so PEG doped and/or organically modified silane (ORMOSIL) derived sol-gels may be considered for the entrapment process. Once entrapment is underway, compounds can be sought for low throughput screening to determine how the SAP-SLAM interaction can be inhibited.

Example 13

GRF-2-Calmodulin Interaction

A further protein candidate for the methods of the present invention is Ras-specific GRF-2, a multidomain protein involved in the activation of intracellular mitogen-activated protein kinases (MAPK) in response to extracellular signals. This protein is of particular interest as it contains an IQ domain which binds calmodulin in response to calcium ions. In addition to the IQ domain, as a certain degree of co-operativity exists within the protein.

Example 14

Polo Box

Another protein—protein interaction which can be advanatgeously studied using the methods of the prresent invention involves the polo kinases. This is a subfamily of protein kinases that are involved in cell cycle control and proliferation and which contain a highly conserved polo-box motif, of 29 amino acid residues, within the non-catalytic c-terminal domain. The native polo-box motif can be studied with a single tryptophan residue at position 5. Trp fluorescence can be used to follow the dimer-monomer transition, and the monomer-random coil transition. The dimer-monomer transition is preferably initiated using GdHCl, and is reversible. The monomer-random coil transition is not reversible. An intact dimer has been successfully entrapped in both TEOS and PGS derived matrices, with and without PEG or bis-silane additives. In all cases, the entrapped dimer can be successfully disrupted and reformed using GdHCl. Ongoing work involves the effect of osmolytes on protein stability, both in solution and entrapped in a sol-gel derived matrix. Future studies will then concentrate on the homo- and hetero-interactions of the polo-box motif.

Example 15

Sol-Gel Materials Development

It has been demonstrated that PEG improves the activity of proteins such as lipase and HSA upon entrapment into TEOS and ORMOSIL derived sol-gels. Similarly, it has been demonstrated that the thermal stability of certain enzymes is improved when encapsulated with sarcosine and sorbitol. Accordingly, such materials may be advantageously used to stabilize the previously discussed protein—protein interactions.

A second route to sol-gel based glasses is a process wherein, ethanol that is generated in the hydrolysis of TEOS (and which is a potent denaturant of proteins) is removed by rotary evaporation, and glycerol is condensed onto the silicate to form a polyglyceryl silicate (PGS). The hydrolysis of PGS occurs at neutral pH, and evolves glycerol, which is a stabilizer of proteins. This approach produces optically clear materials containing biomolecular interactions.

Different precursors are available to entrap protein—protein complexes, namely in the area of silane precursor synthesis. A small number of bis-silanes, predominantly based on two triethoxysilanes tethered by a propyl or propyl ether chain have been prepared. Incorporating the bis-silane into sol-gel precursor mixes at levels of 5–10% is useful in both preparation of thin films as well as for maintaining the activity of entrapped proteins. While not wishing to be bound by any particular theory, it is our hypothesis that the bis-silanes aid in controlling the pore sizes of the silicate matrix. Control over the pore sizes enables disruption of protein—protein interactions without steric interference from the matrix.

Example 16

New Interaction Systems

New protein—protein interaction systems may be investigated using a variety of fluorescence methods including intensity, anisotropy and lifetime. Further, each is amenable to labelling, either with 7-azatryptophan or with an extrinsic label.

Each of the protein—protein interaction systems may be tested using known disruptors (as for TFP with CaM: Melittin) and analogs. Mixtures of known inhibitors and non-inhibitors may also be examined to determine if the assay can identify inhibitors in mixtures, as might be required when screening natural product libraries. In addition, "arrays" of entrapped protein—protein interactions can be deposited onto glass slides using manual deposition techniques (i.e., by pipetting small drops silica containing different complexes onto the slide) or automated deposition methods (stamping, inkjet deposition, screen printing). These may be able to be sampled by moving an optical fiber over each element to detect if disruption of multiple complexes can be done simultaneously, or by imaging with a CCD camera.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

Reversibility of disruption for entrapped BCaM:melittin.

|  | Relative Intensity | Anisotropy | Wavelength Maximum |
|---|---|---|---|
| Native | 100 | 0.129 | 334 nm |
| Denatured | 40 | 0.099 | 346 nm |
| Recovered | 104 | 0.136 | 330 nm |

TABLE 2

|  | Anisotropy | Wavelength (nm) |
|---|---|---|
| Native | 0.129 | 334 |
| Denatured | 0.099 | 346 |
| Recovered with no TFP | 0.136 | 331 |
| Denatured, TFP added | 0.115 | 346 |
| Recovered with TFP | 0.121 | 346 |

TABLE 3

Fluorescence lifetime data for B-CaM:dansyl-Melittin

| Sample | $f_1$ | $f_2$ | $f_3$ | $\tau_1$ | $\tau_2$ | $\tau_3$ | $<\tau>$ | $\chi^2$ |
|---|---|---|---|---|---|---|---|---|
| Dan-Mel | 0.898 | 0.102 | — | 9.898 | 1.029 | — | 8.992 | 1.07 |
| DM:B-CaM (native) | 0.535 | 0.426 | 0.038 | 48.05 | 7.666 | 1.211 | 29.03 | 1.11 |
| DM:B-CaM (recovered with TFP) | 0.664 | 0.336 | — | 13.57 | 2.685 | — | 9.92 | 1.23 |

$f_i$ = fractional fluorescence of component i, $\tau_i$ = lifetime of component i, $<\tau> = \Sigma f_i \tau_i$

We claim:

1. A carrier comprising a matrix of an inorganic glass or a hybrid organic-inorganic glass, wherein the matrix contains complex of two or more biological species entrapped within the matrix, wherein the complex is formed before entrapment in the matrix and comprises two or more biological species that can be reversibly dissociated from the other under dissociating conditions, wherein the biological species are selected from the group consisting of proteins, polypeptides, peptides, amino acids, DNA, RNA and phospholipids and wherein the carrier has a pore size that is selected to inhibit leaching out of the complex of two or more biological species or biological species thereof.

2. The carrier of claim 1 wherein the biological species of the complex can under denaturing conditions be reversibly disrupted within the matrix and wherein the matrix in the denaturing conditions inhibits aggregation of the biological species.

3. The carrier of claim 2 wherein pore size of the carrier is selected to enable potential modulators of the complex to pass in and out of the matrix.

4. The carrier of claim 1 wherein the biological species complex of the can under naturing conditions associate with one another.

5. The carrier of claim 4 wherein the association between the biological species under naturing conditions is selected from the group consisting of one or more of: ionic bonds, hydrogen bonds, van der Waal's intractions, hydrophobic interactions, dipole—dipole interactions, dipole-induced dipole interactions and induced dipole-induced dipole interactions.

6. The carrier of claim 4 wherein pore size of the carrier is selected to enable potential modulators of the complex to pass in and out of the matrix.

7. The carrier according to claim 1 wherein the carrier comprises a silica based glass.

8. The carrier according to claim 1 wherein the inorganic material is selected from the group consisting of a silicon, titanium, vanadium cerium-based metal alkoxide, cerium-based metal alkoxide, alkylated metal alkoxide, an otherwise functionalized metal alkoxide, a corresponding metal chloride, silazane, polyglycerylsilicate and other silicate precursor.

9. The carrier according to claim 1 derived by a sol-gel processing method.

10. The carrier according to claim 9 wherein the complex is bioactive.

11. The carrier according to claim 10 wherein the carrier is pretreated to contain components found in an animal fluid.

12. The carrier according to claim 11 wherein the pretreatment is by immersion in a solution containing components found in an animal fluid for a period of up to about seven days prior to use.

13. The carrier according to claim 12 wherein the animal fluid is interstitial fluid.

14. The carrier according to claim 13 wherein the carrier is synthesized under sterile conditions or sterilized subsequent to synthesis using conventional sterilization methods.

15. The carrier according to claim 9, wherein the carrier is formed into spots on a surface of a solid support.

16. The carrier according to claim 15, wherein the spots are formed by pin spotting, stamping, inkjet methods or screen printing.

17. The carrier according to claim 15, wherein the spots on the surface of the solid support form an array.

18. The carrier according to claim 1, wherein the carrier is formed into spots on a surface of a solid support.

19. The carrier according to claim 18, wherein the spots are formed by pin spotting, stamping, inkjet methods or screen printing.

20. The carrier according to claim 18, wherein the spots on the surface of the solid support form an array.

* * * * *